(12) United States Patent
Paydarfar et al.

(10) Patent No.: US 10,506,983 B2
(45) Date of Patent: Dec. 17, 2019

(54) APPLICATION OF THE EXTREMA DISTORTION METHOD TO OPTIMIZE CONTROL SIGNALS

(71) Applicant: University of Massachusetts Medical School, Boston, MA (US)

(72) Inventors: David Paydarfar, Newton, MA (US); Joshua Chang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 164 days.

(21) Appl. No.: 15/715,113

(22) Filed: Sep. 25, 2017

(65) Prior Publication Data

US 2018/0192961 A1   Jul. 12, 2018

Related U.S. Application Data

(63) Continuation of application No. PCT/US2016/024464, filed on Mar. 28, 2016.

(60) Provisional application No. 62/139,014, filed on Mar. 27, 2015.

(51) Int. Cl.
| | | |
|---|---|---|
| *A61B 5/00* | (2006.01) | |
| *A61B 5/04* | (2006.01) | |
| *A61M 21/00* | (2006.01) | |

(52) U.S. Cl.
CPC ........ *A61B 5/7235* (2013.01); *A61B 5/04001* (2013.01); *A61B 5/4094* (2013.01); *A61B 5/7203* (2013.01); *A61M 2021/0055* (2013.01)

(58) Field of Classification Search
CPC . A61B 5/7235; A61B 5/04001; A61B 5/4094; A61B 5/7203; A61M 2021/0055
See application file for complete search history.

(56) References Cited

U.S. PATENT DOCUMENTS

| | | | |
|---|---|---|---|
| 5,311,001 A | 5/1994 | Joseph et al. | |
| 5,813,993 A | 9/1998 | Kaplan et al. | |
| 8,755,879 B2* | 6/2014 | Hang | A61B 5/1036 600/545 |
| 2014/0107520 A1 | 4/2014 | Hang et al. | |
| 2014/0195988 A1* | 7/2014 | Kramer | G06F 3/017 715/863 |

OTHER PUBLICATIONS

International Search Report in parent IA No. PCT/US16/24464, dated Jul. 5, 2016.
Written Opinion in parent IA No. PCT/US16/24464, dated Jul. 5, 2016.
(Continued)

*Primary Examiner* — Bryan Bui
(74) *Attorney, Agent, or Firm* — Milstein Zhang & Wu LLC

(57) ABSTRACT

A system is described that observes a signal from a subject of interest, converts the signal to an electrical representation, uses the electrical representation to compute a synthetic control signal, and applies the synthetic control signal to control some aspect of operation of the subject. The procedure used to generate the synthetic control signal involves subjecting the electrical representation of the observed signal to random noise, allowing the extrema of the electrical representation to move, and obtaining a converged solution as the synthetic control signal.

5 Claims, 22 Drawing Sheets

(56) References Cited

OTHER PUBLICATIONS

Szeliski, "Computer Vision: Algorithms and Applications", Electronic draft, Sep. 3, 2010, Springer.
Chang et ai, "Flipping Biological Switches: Solving for Optimal Control: A Dissertation", University of Massachusetts Medical School, Mar. 30, 2015.

* cited by examiner

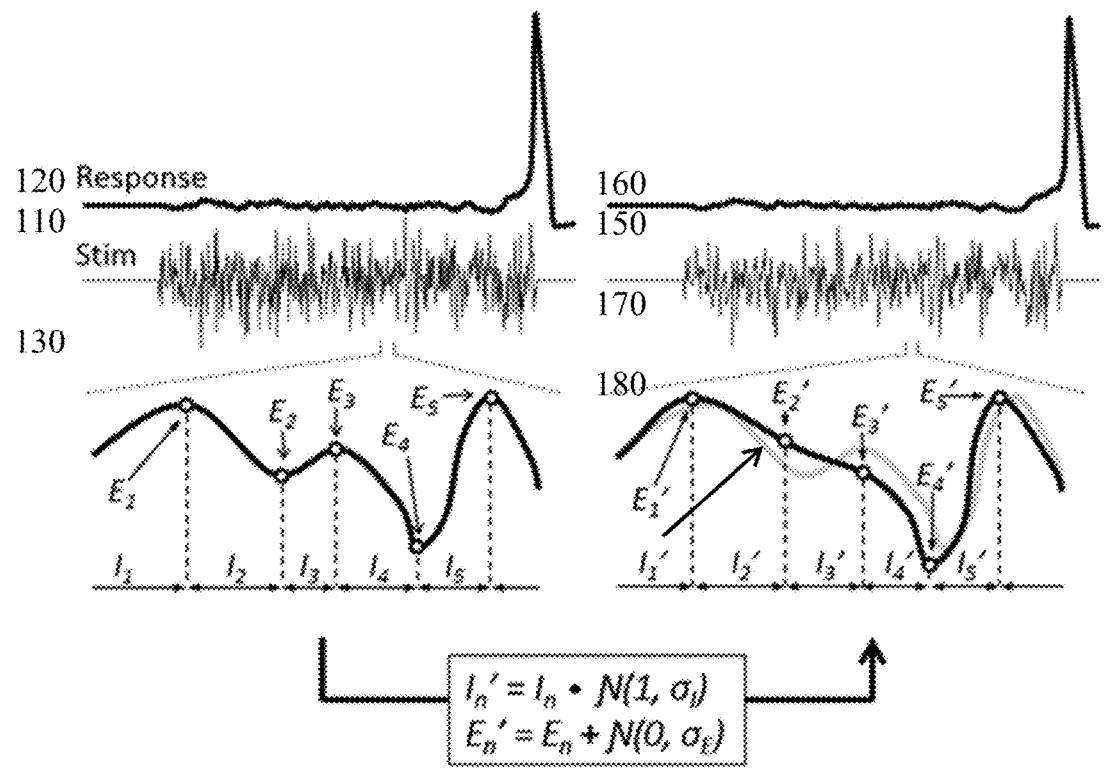
FIG. 1A  FIG. 1C
FIG. 1B
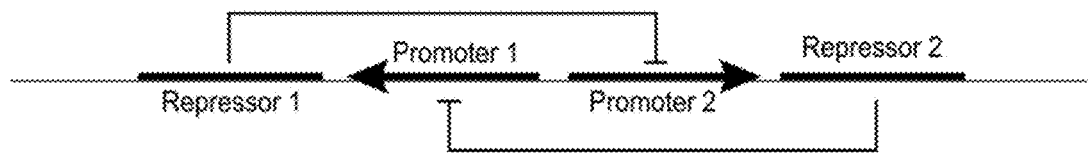
FIG. 2

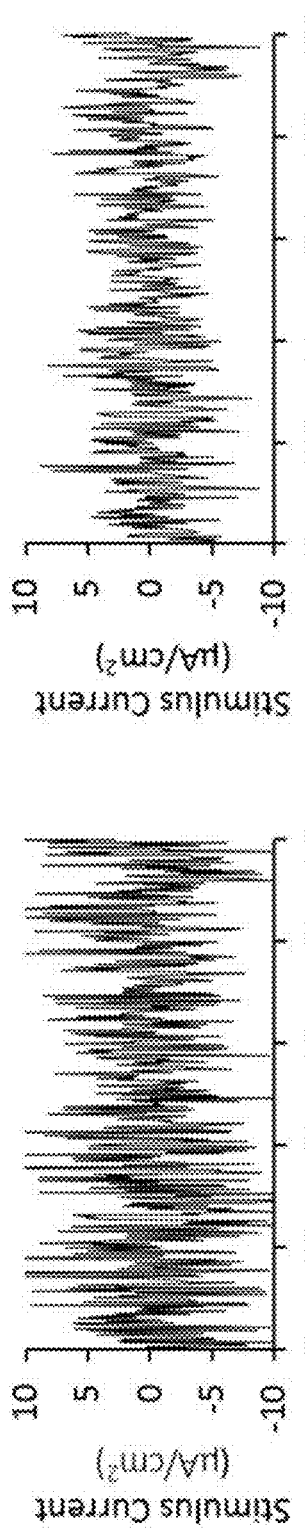
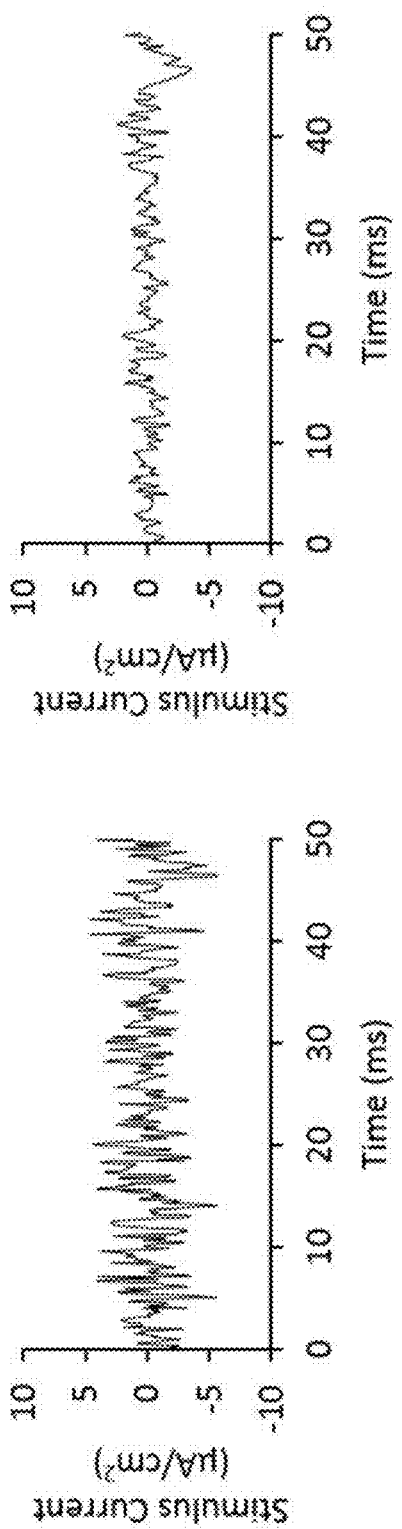

FIG. 4A
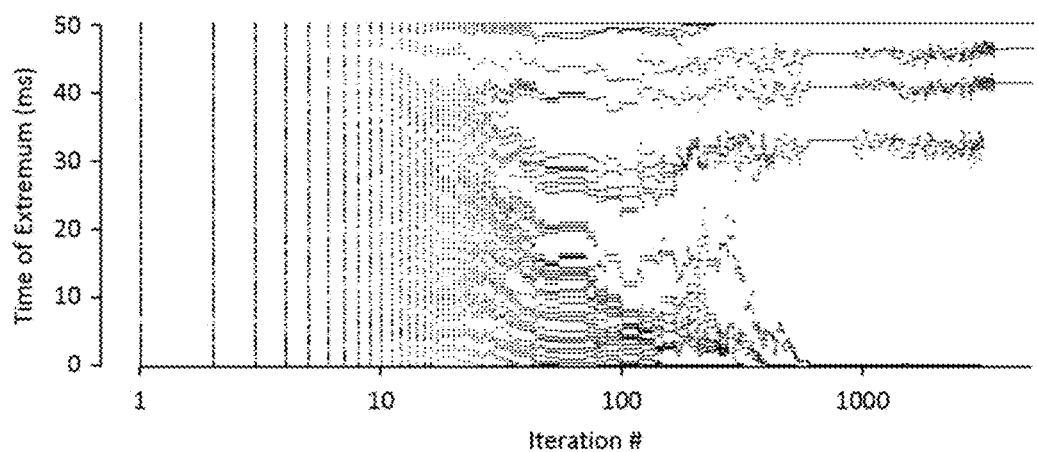
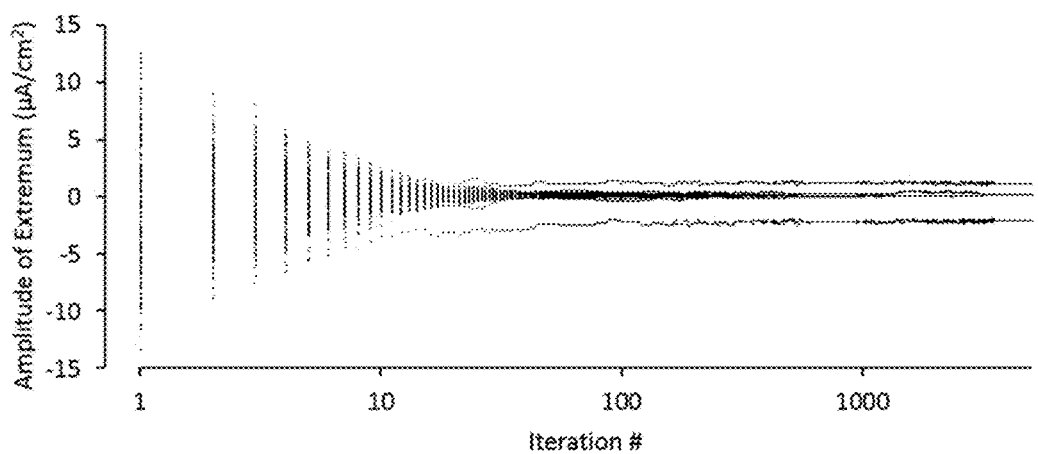
FIG. 4B

FIG. 5A
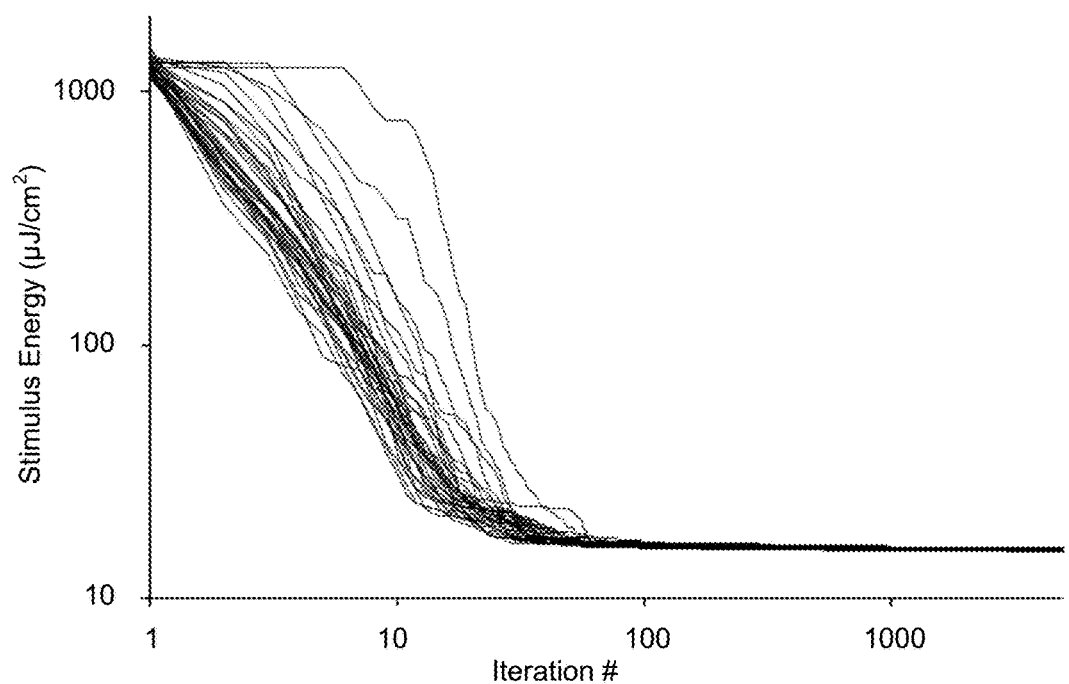
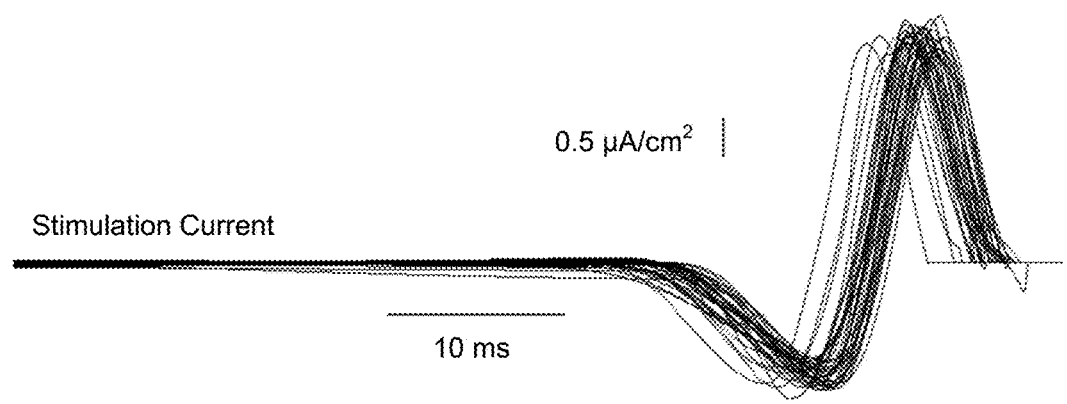
FIG. 5B

FIG. 6A
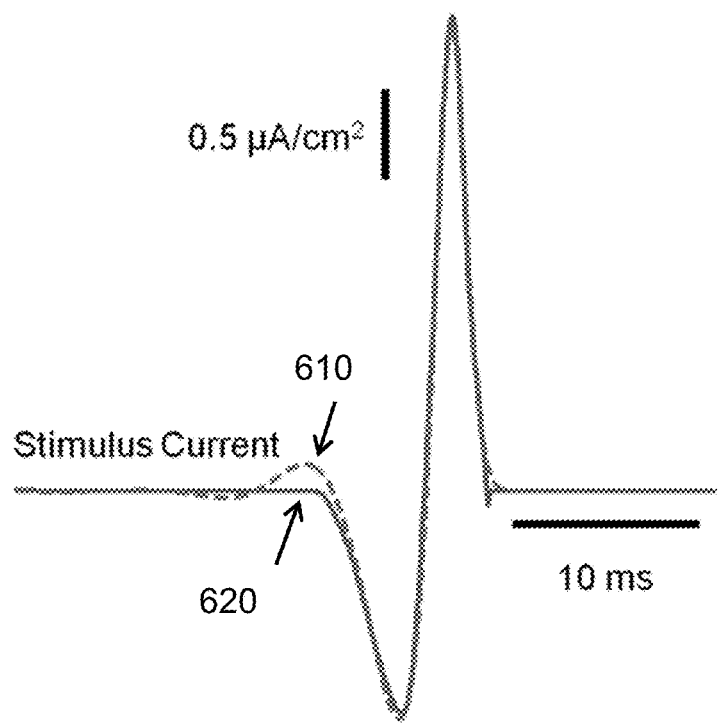
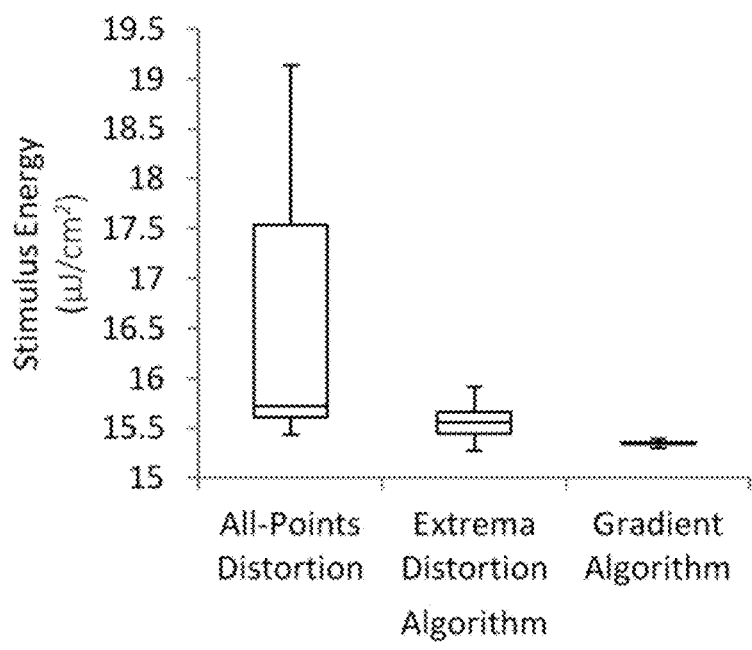
FIG. 6B

FIG. 8A
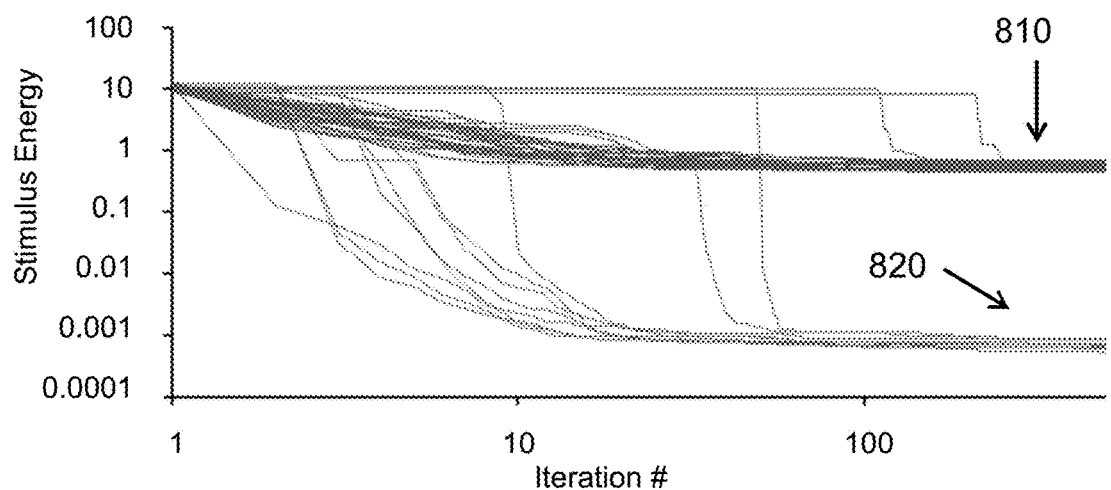
FIG. 8B
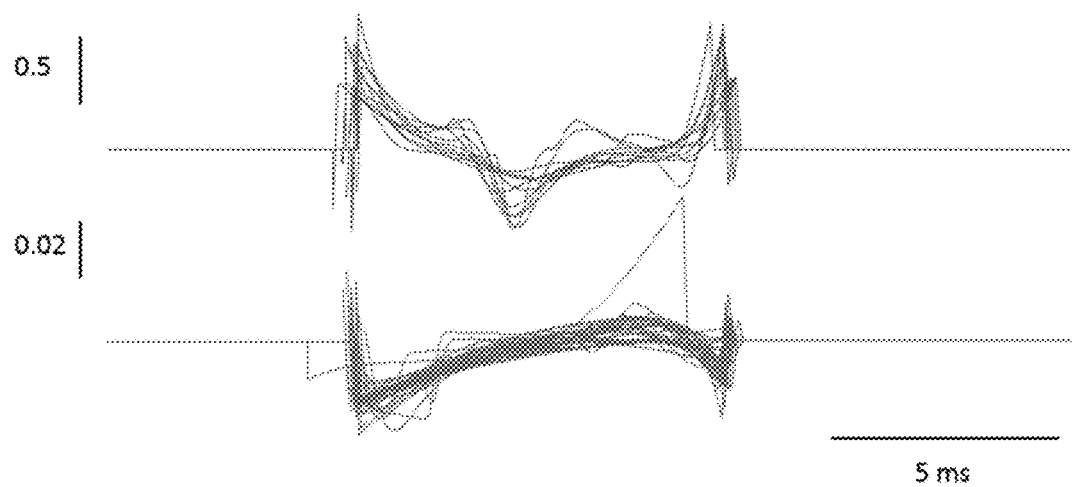
FIG. 8C

FIG. 9A
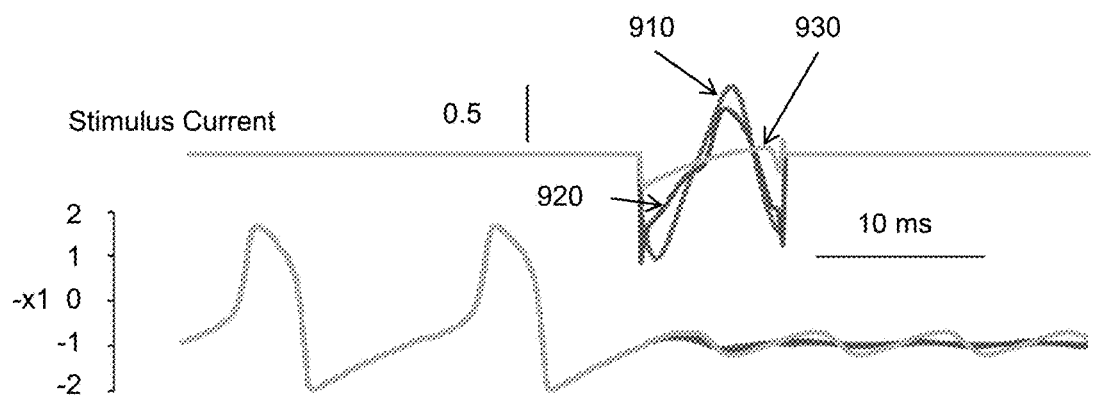
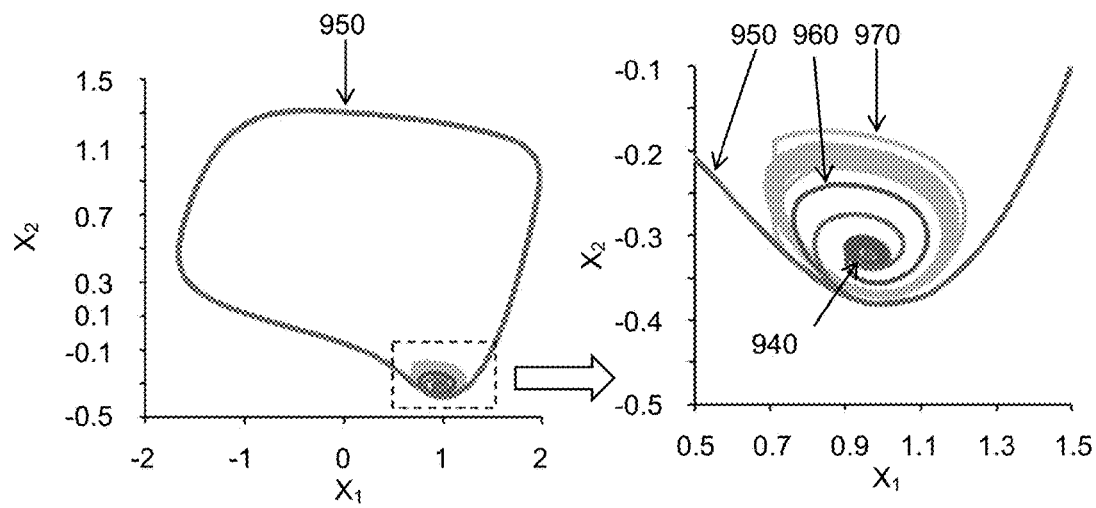
FIG. 9B　　　　　　　　FIG. 9C

FIG. 10A
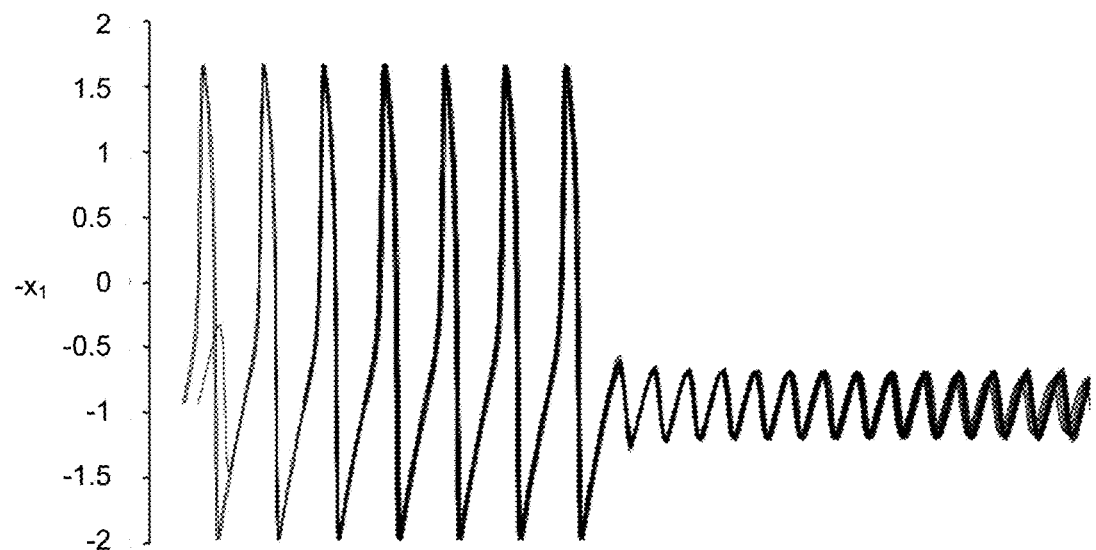
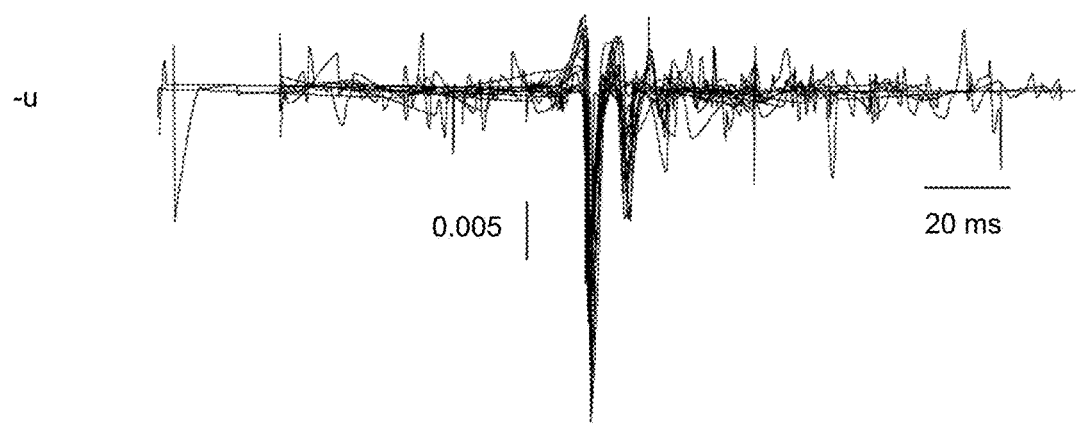
FIG. 10B

FIG. 11A
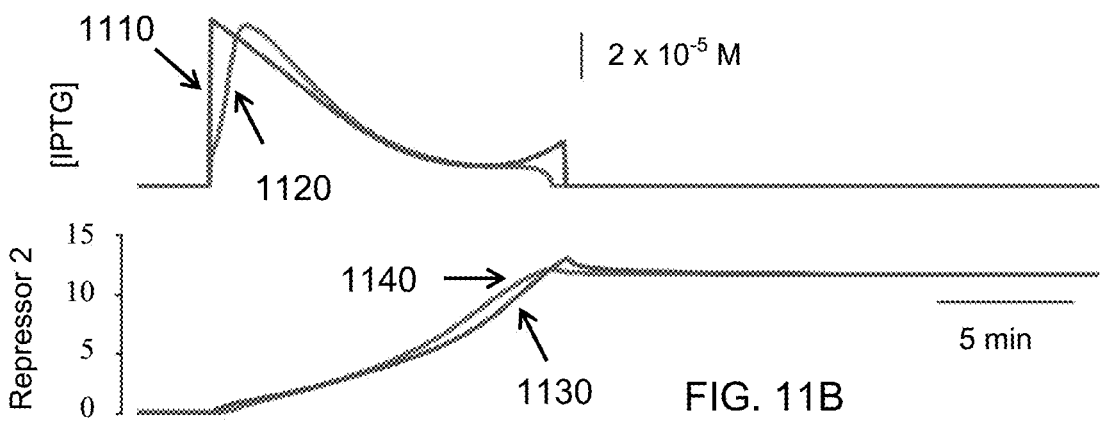
FIG. 11B
FIG. 11C
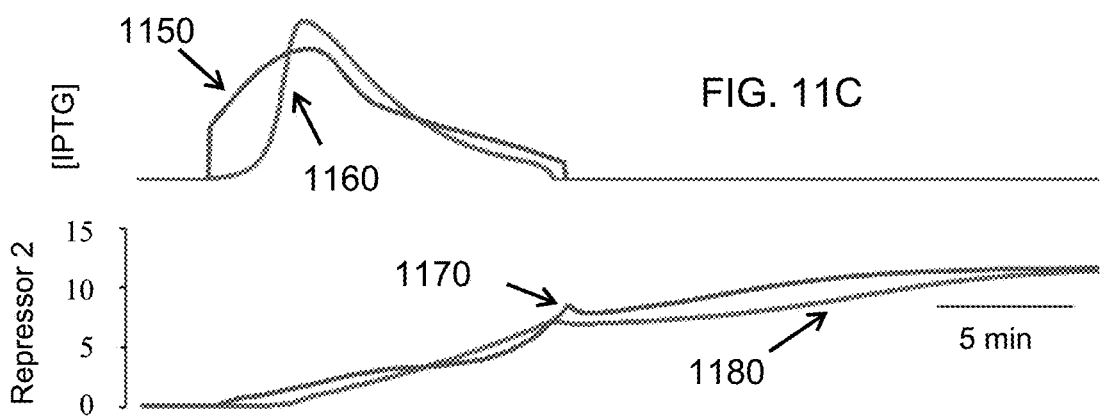
FIG. 11D

FIG. 16A
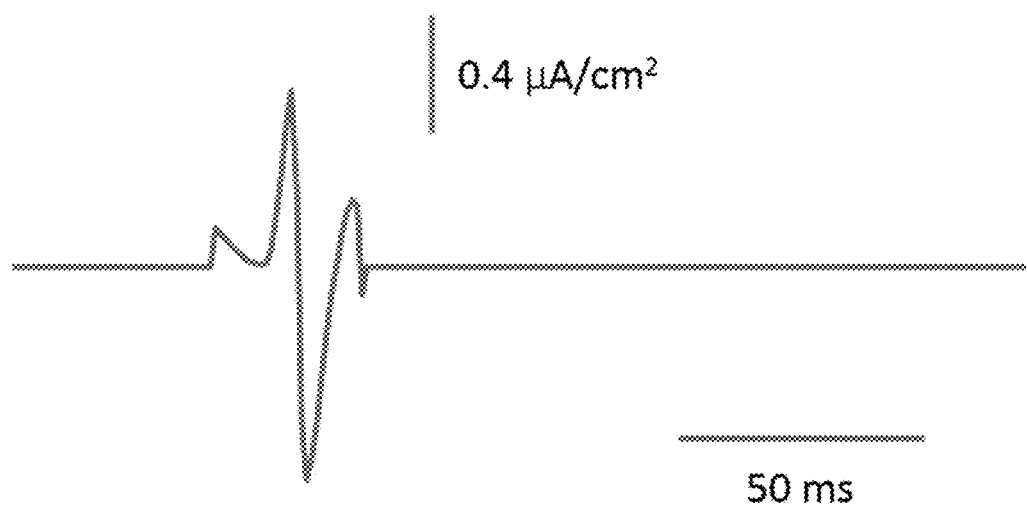
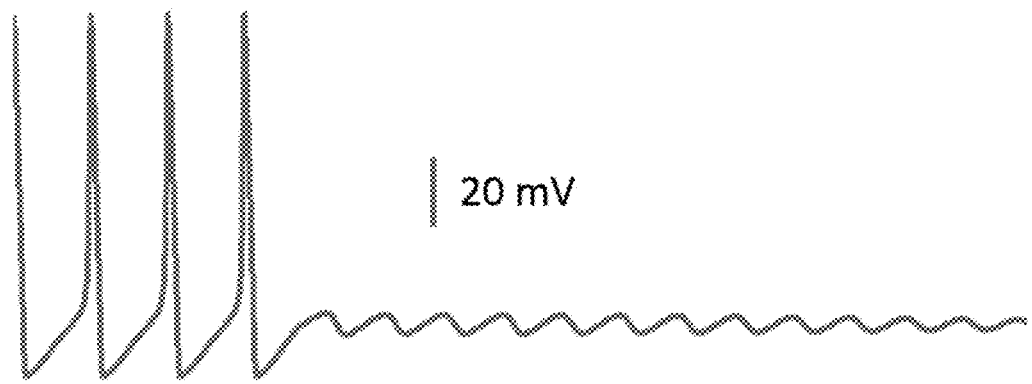
FIG. 16B

FIG. 17A
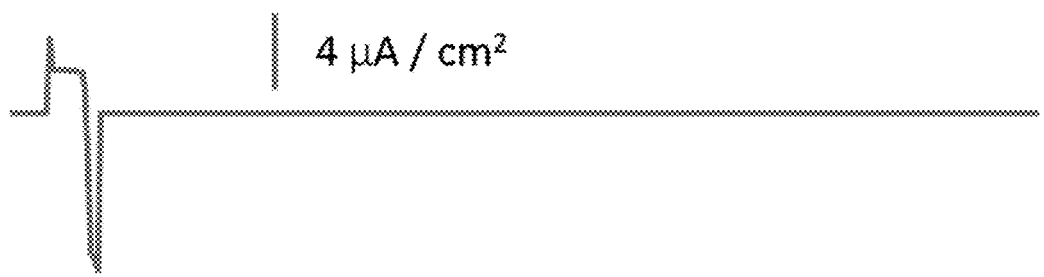
FIG. 17B
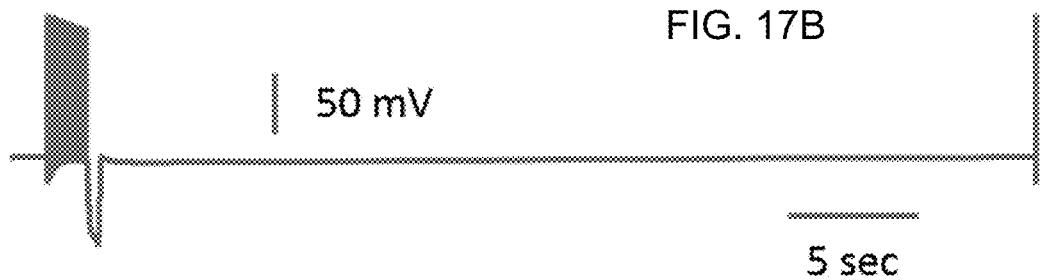
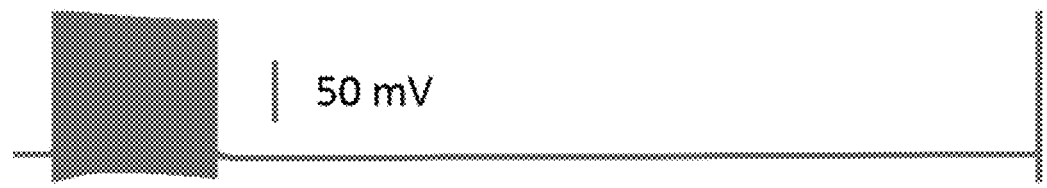
FIG. 17C

FIG. 19A
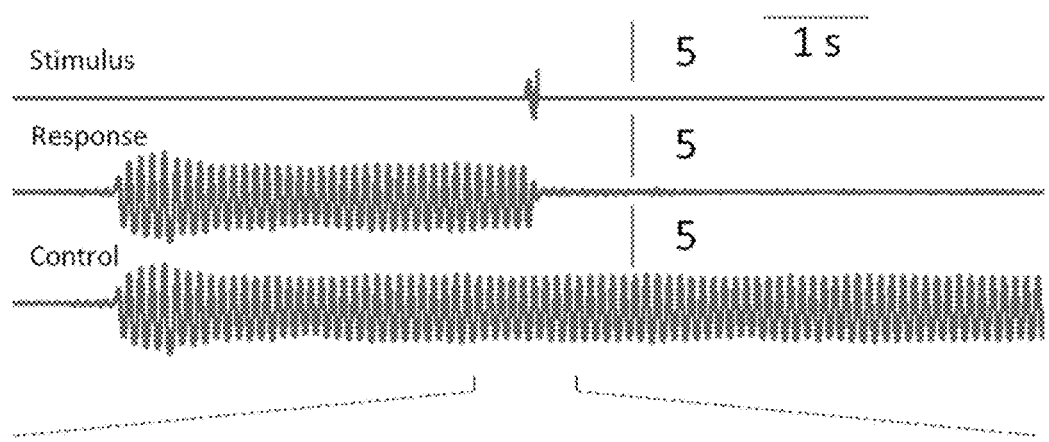
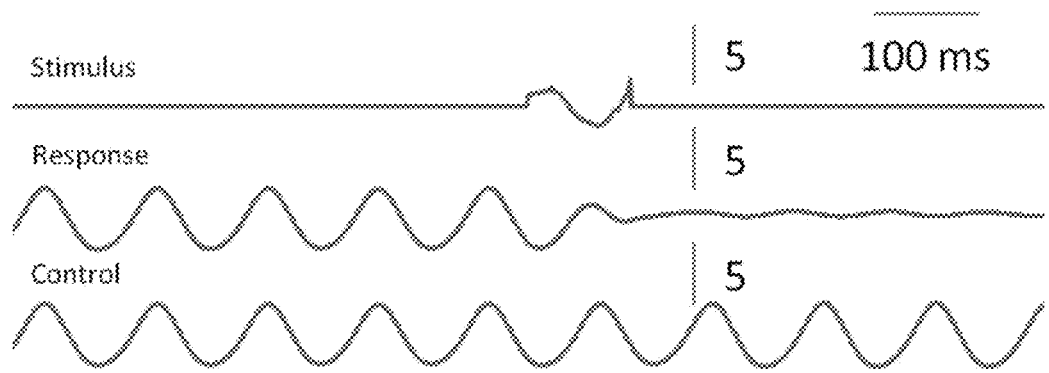
FIG. 19B

APPLICATION OF THE EXTREMA DISTORTION METHOD TO OPTIMIZE CONTROL SIGNALS

CROSS-REFERENCE TO RELATED APPLICATIONS

This application is a continuation of co-pending International Patent Application No. PCT/US16/24464, filed Monday, Mar. 28, 2016, which application in turn claims priority to and the benefit of then co-pending U.S. provisional patent application Ser. No. 62/139,014, filed Mar. 27, 2015, which application is incorporated herein by reference in its entirety.

STATEMENT REGARDING FEDERALLY FUNDED RESEARCH OR DEVELOPMENT

This invention was made with government support under R01 GM104987 awarded by the National Institutes of Health. The government has certain rights in the invention.

FIELD OF THE INVENTION

The invention relates to control signal methods in general and particularly to systems and method of generating control signals.

BACKGROUND OF THE INVENTION

Many systems for controlling objects are known in the art. There is a need for improved control systems.

SUMMARY OF THE INVENTION

According to one aspect, the invention features a system for controlling a signaling pathway in a subject of interest. The system comprises a sensor configured to observe a signal in the subject of interest, and configured to provide an electrical representation of the signal for further manipulation; a module configured to accept as input the electrical representation of the signal for further manipulation, configured to apply the Extrema Distortion Algorithm to the electrical representation of the signal, configured to generate a synthetic control signal, and configured to provide the synthetic control signal as an output; and a signal application module configured to receive the synthetic control signal and configured to apply the synthetic control signal to the subject of interest.

According to one aspect, the invention features a system for controlling a signaling pathway in a subject of interest, comprising: a sensor configured to observe a signal in the subject of interest, and configured to provide an electrical representation of the signal for further manipulation; a module configured to accept as input the electrical representation of the signal for further manipulation; a module configured to apply the Extrema Distortion Algorithm to the electrical representation of the signal, and configured to generate a synthetic control signal; a module configured to provide the synthetic control signal as an output; and a signal application module configured to receive the synthetic control signal and configured to apply the synthetic control signal to the subject of interest.

In one embodiment, the sensor configured to observe a signal is configured to provide the electrical representation in the form of an analog signal having an amplitude and a phase.

In another embodiment, the sensor configured to observe a signal is configured to provide the electrical representation in the form of in the form of a plurality of discrete time based signals, each discrete signal having an amplitude and an identifier indicating the position of the signal in a time sequence.

In yet another embodiment, the module configured to accept as input the electrical representation is a data acquisition module.

In still another embodiment, the module configured to apply the Extrema Distortion Algorithm is a general purpose programmable computer which when operating under control of instructions recorded on a non-volatile medium is configured to perform the steps of the Extrema Distortion Algorithm.

In a further embodiment, the Extrema Distortion Algorithm (EDA) includes instructions recorded on the non-volatile medium that are configured to direct the general purpose computer to:

a. Select a randomly generated starting seed that successfully causes a state transition.
b. Find the extrema of the starting seed and measure the time interval between them.
c. Multiply each of the time intervals by a randomly generated number (e.g. with a Gaussian distribution).
d. Rescale the time of the synthetic stimulus to match the duration of the original stimulus.
e. Add to each peak a randomly generated number (e.g. with a Gaussian distribution).
f. Linearly transform all the data points between the extrema with the new extrema endpoints.
g. Test the distorted stimulus in the system, checking to see if it achieves pre-specified constraints.
h. Calculate the performance metric (e.g. $L^2$-norm) of each of the neighboring stimuli
i. Repeat steps c.-h. N times to produce N neighboring solutions based on the starting seed.
j. Choose the stimulus from among the neighboring solutions and the starting seed with the best performance.
k. Repeat steps b.-j. for a predetermined number of times M each iteration using the best stimuli found from the previous iteration as the new starting seed in step b.
l. After M iterations, output the stimulus with the best performance metric as the optimal stimulus.

In yet a further embodiment, the module configured to provide the synthetic control signal as an output is a data acquisition module having a data output port.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1A is a diagram of an input stimulus 110 applied to a system and a response signal 120 that the system produces. The signal 130 is a detailed view of a segment of the input signal 110, which is a piecewise smooth continuous signal.

FIG. 1B is a schematic diagram illustrating one embodiment of the Extrema Distortion Algorithm in operation. In operation, the extrema of the input signal are determined, and the intervals as well as the amplitudes are then distorted using multiplicative and addictive noise respectively to generate a new signal.

FIG. 1C is a diagram of a synthetic input 130 and the response signal 140 that is observed when the synthetic input is applied to the same system. In FIG. 1C, the signal 170 is the resultant piecewise smooth signal over an interval similar to that for signal 130, and signal 180 is a copy of the input signal 130 shown for comparison.

FIG. 2 is a diagram of the genetic toggle switch, including Promoter 1, promoter 2, Repressor 1 and Repressor 2. FIG. 2 is adapted from Gardner T S, Cantor C R, Collins J J (2000) Construction of a genetic toggle switch in *Escherichia coli*. Nature 403: 339-342.

FIG. 3A through FIG. 3H illustrate the progression of waveforms that occur in applying the Extrema Distortion Algorithm. As illustrated in FIG. 3A through 3H, the Extrema Distortion Algorithm shapes stochastically generated stimuli towards an optimal waveform. FIG. 3A through 3H illustrate the progression of solutions from the original white noise stimulus in the $1^{st}$ iteration to the $2^{nd}$, $5^{th}$, $10^{th}$, $20^{th}$, $50^{th}$, $1000^{th}$ and $5000^{th}$ iteration, respectively. By convention, positive current is depolarizing.

FIG. 4A is a diagram that shows the timing of the extrema as a function of iteration number.

FIG. 4B is a diagram that shows the amplitude of the extrema as a function of iteration number.

FIG. 5A is a diagram that shows the progression of improvement in stimulus energy over the 5,000 iterations for 35 snippets.

FIG. 5B is a diagram that shows the resulting stimuli for all 35 snippets.

FIG. 6A is a graph that shows a result from the best of the 35 snippets using distortion of the extrema (curve 620) as compared to the best of the 35 snippets using distortion of all the points (610).

FIG. 6B is a graph that shows the range of stimulus energy in 35 runs of both the Extrema Distortion Algorithm as well as the gradient algorithm. The stimulus' baseline is at 0 $\mu A/cm^2$.

FIG. 8A is a graph showing that the Extrema Distortion Algorithm converges towards the two locally optimal solutions in the FitzHugh-Nagumo model, with the model response curves 810 corresponding to the stimuli shown in FIG. 8B and the response curves 820 corresponding to the stimuli shown in FIG. 8C.

FIG. 8B is a graph of a first set of stimuli.

FIG. 8C is a graph of a second set of stimuli, which are much smaller in scale than the stimuli shown in FIG. 8B. The snippets are aligned such that the first valley after repetitive firing has ended occurs at 0 ms. The stimulus' baseline is at zero.

FIG. 9A is a graph showing stimuli that result from the gradient algorithm (curve 910) as well as two versions of the Extrema Distortion Algorithm. The first version of the Extrema Distortion Algorithm (curve 920) limits the terminal condition of success to be extremely close to the fixed point similar to the gradient algorithm. The second version of the Extrema Distortion Algorithm (curve 930) specifies the condition of success to just be a suppression of action potentials ($-x_1 < 1.5$).

FIG. 9B shows the state space of the system's response to the various stimuli. The stimulus's baseline is at 0.

FIG. 9C shows an expanded view of a region shown in FIG. 9B next to the fixed point 940. Curves 950, 960 and 970 are the responses to stimuli 910, 920 and 930, respectively.

FIG. 10A is a graph showing a response of the FitzHugh-Nagumo model. The Extrema Distortion Algorithm can be used to gain insight into the phase-dependency and duration of the optimal stimulus. The Extrema Distortion Algorithm used on 17 unique 100-ms snippets shows converge towards a phase-specific stimulus waveform. These snippets were all aligned such that the first peak after the action potential occurred at 100 ms.

FIG. 10B is a graph of the stimulus that generated the response shown in FIG. 10A. The stimulus's baseline is at 0.

FIG. 11A is a graph of a stimulus in terms of concentration of [IPTG] as a function of time for the Extrema Distortion Algorithm (curve 1110) and for the gradient algorithm (curve 1120). The stimulus starts at 0 M [IPTG].

FIG. 11B is a graph of the concentration of Repressor 2, [Repressor 2] as a function of time for the Extrema Distortion Algorithm (curve 1130) and for the gradient algorithm (curve 1140). The algorithms produce very similar waveforms. Success is defined by seeing a transition occur at 20 minutes.

FIG. 11C is a graph of a stimulus in terms of concentration of [IPTG] as a function of time for the Extrema Distortion Algorithm (curve 1150) and for the gradient algorithm (curve 1160), The stimulus starts at 0 M [IPTG].

FIG. 11D is a graph of the concentration of Repressor 2, [Repressor 2] as a function of time for the Extrema Distortion Algorithm (curve 1170) and for the gradient algorithm (curve 1180). The algorithms produce very similar waveforms. Success defines the transition occurring at 100 minutes, while the stimulus duration is still kept at 20 minutes. The gradient algorithm calculates the optimal stimulus using knowledge of where the separatrix, while the Extrema Distortion Algorithm does not.

FIG. 16A is a graph of an optimal stimulus waveform for suppressing repetitive firing in a single cell as a function of time.

FIG. 16B is a graph of the response as a function of time.

FIG. 17A is a graph of an optimal 2 second stimulus waveform for suppressing repetitive firing in a single cell burster as a function of time.

FIG. 17B is a graph of the response as a function of time when the optimal stimulus is given.

FIG. 17C is a graph of the response as a function of time when no stimulus is given.

FIG. 19A is a graph showing the stimulus, the system's response, and the control response with no stimulus for an optimal stimulus waveform for suppressing seizure activity in a systemic population-based model.

FIG. 19B is a graph showing a detailed view of the transition due to the stimulus shown in FIG. 19A.

DETAILED DESCRIPTION

Stochastic Extrema Distortion Algorithm

Figure 3E:
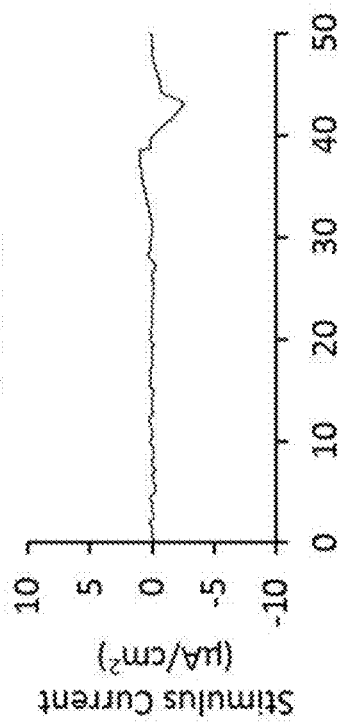
Figure 3F:
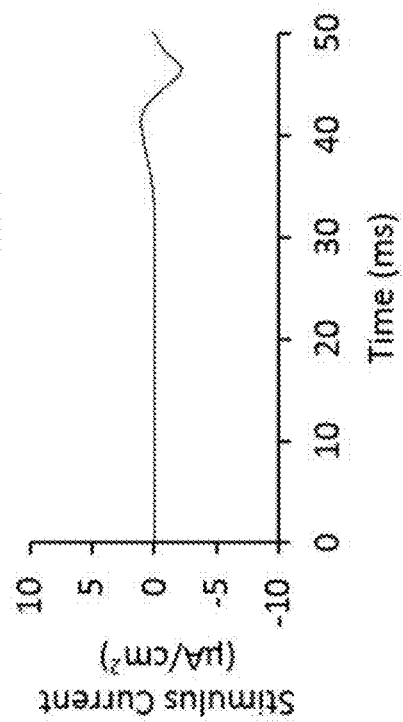
Figure 3G:
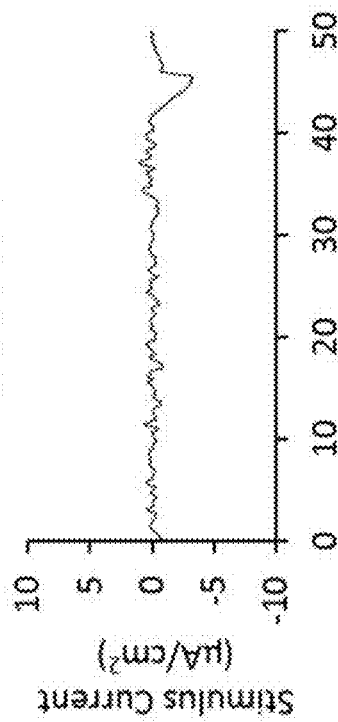
Figure 3H:
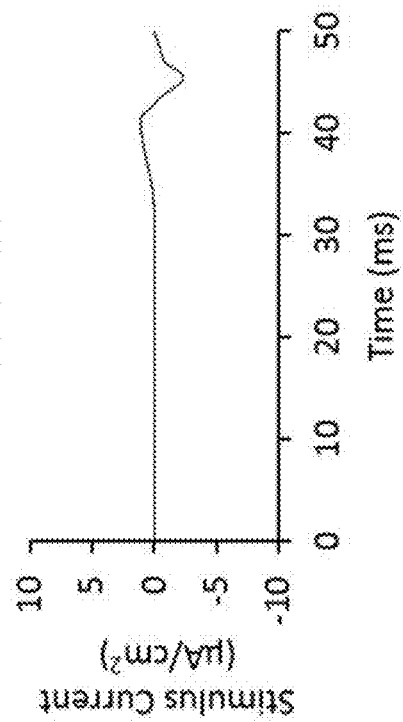

The systems that are described include a subject (which may be a biological entity, a mechanical device, an electro-mechanical device and the like, or a mathematical model that renders features of a subject) that generates a signal that can be sensed, and is understood to relate to some aspect of the system that is to be controlled or regulated. The sensed signal is used as input, which is subjected to analysis and a synthetic control signal is generated. The synthetic control signal is applied to the system to control that aspect of the system requiring improved control. The method can be operated on a system that does not have a known mathematical model, or has a mathematical model that is too complicated to yield information about an appropriate control signal based on the input signal. The invention has been tested and demonstrated to operate correctly in a number of systems that are biological in nature. In various embodiments, the systems and methods of the invention can be used with feedback. In various embodiments, the systems and methods of the invention can be used in feedforward mode, without feedback. The systems and methods of the invention have been observed to be operable on a single subject, where there is no a priori knowledge of the subject history (e.g., there is not sufficient prior information about that individual subject on which to base a control strategy) and where there may not be a well understood body of data that can be used to provide "rules of thumb" or guidance based on aggregated data from many similar subjects.

The stochastic Extrema Distortion Algorithm is based on the idea of allowing each extremum to move randomly, using a linear transformation of the original signal with the new extrema as endpoints to fill in the gaps in between extrema.

FIG. 1A is a diagram of an input stimulus 110 applied to a system and a response signal 120 that the system produces. The signal 130 is a detailed view of a segment of the input signal 110, which is a piecewise smooth continuous signal.

FIG. 1B is a schematic diagram illustrating one embodiment of the EDA in operation. In operation, the extrema of the input signal are determined, and the intervals as well as the amplitudes are then distorted using multiplicative and additive noise respectively to generate a new signal.

FIG. 1C is a diagram of a synthetic input 130 and the response signal 140 that is observed when the synthetic input is applied to the same system. In FIG. 1C, the signal 170 is the resultant piecewise smooth signal over an interval similar to that for signal 130, and signal 180 is a copy of the input signal 130 shown for comparison.

As illustrated in FIG. 1A through FIG. 1C, the extrema are determined, and the intervals as well as the amplitudes are then distorted using multiplicative and additive noise respectively to generate a new signal.

The steps of the algorithm related to FIG. 1A-FIG. 1C are as follows:

a. Select a randomly generated starting seed that successfully causes a state transition.

b. Find the extrema of the starting seed and measure the time interval between them.

c. Multiply each of the time intervals by a randomly generated number (e.g. with a Gaussian distribution).

d. Rescale the time of the synthetic stimulus to match the duration of the original stimulus.

e. Add to each peak a randomly generated number (e.g. with a Gaussian distribution).

f. Linearly transform all the data points between the extrema with the new extrema endpoints.

g. Test the distorted stimulus in the system, checking to see if it achieves pre-specified constraints.

h. Calculate the performance metric (e.g. $L^2$-norm) of each of the neighboring stimuli i. Repeat steps c.-h. N times to produce N neighboring solutions based on the starting seed.

j. Choose the stimulus from among the neighboring solutions and the starting seed with the best performance.

k. Repeat steps b.-j. for a predetermined number of times M each iteration using the best stimuli found from the previous iteration as the new starting seed in step b.

l. After M iterations, output the stimulus with the best performance metric as the optimal stimulus.

The following are all user-defined parameters: the variance of the Gaussian distributions used to distort amplitudes and inter-extrema intervals, the number of neighboring stimuli generated for each iteration, and the number of iterations used before ending the algorithm. These parameters can be empirically tuned to optimize computational performance of the algorithm.

We believe that the rate of convergence, computational efficiency, and accuracy of EDA would improve by using: i) non-Gaussian extrema distortion, ii) non-linear extrapolation between extrema, iii) adaptive learning methods to modify the statistics of distortion from one iteration to the next.

The algorithm detailed above results in the energy-optimal electrical stimulus waveform for causing a single action potential. Other applications may require defining a different optimization metric, which can include multiple performance measures. For instance if we are seeking the most energy-optimal stimulus that maximally desynchronizes a group of neurons, then the optimization metric would combine two performance measures: $L^2$-norm of the stimulus and a desynchronization index.

In the algorithm detailed above we fed white noise stimuli into the system in order to capture only the snippets that caused a state transition. These snippets became the starting seeds for our algorithm. Depending on the performance measure chosen, the starting seeds may not need to cause a state transition.

Using the EDA we have computed optimal stimulus waveforms that flip the following mathematical models of biological switches:
1. Flipping a genetic toggle switch
2. Induction of an action potential
3. Suppression of a pacemaker cell underlying epileptic seizures
4. Desynchronization of an epileptic network of cells
5. Switching off whole brain epileptic activity Other medical applications for which EDA may be used to optimized a response are believed to include:
1. Electrical stimuli from devices implanted in the body
   a. Defibrillators
   b. Dual chamber and single chamber pacemakers
   c. Deep brain stimulators for neurological disorders including parkinsonism, epilepsy, memory disorders, psychiatric disorders
   d. Cortical stimulators for the same
   e. Spinal stimulators for pain, paralysis, bladder dysfunction
   f. Peripheral nerve stimulators for epilepsy, pain, bladder dysfunction obesity, paralysis, sensory impairment (e.g., hearing, vision, tactile, proprioception), and psychiatric disorders
   g. Gastric and intestinal stimulators for gastrointestinal motility disorders
2. Electrical or magnetic stimuli using devices external to the body to treat neurological and psychiatric disorders
3. Biochemical stimuli
   a. Insulin pumps used to control blood sugar
   b. Chemotherapy protocols
   c. Immunization protocols
   d. Oxygen administration during respiratory failure
4. Phototherapeutic stimuli for circadian and psychiatric disorders.
5. Mechanical stimuli to enhance physiological functions (e.g., breathing, balance, gait, sleep)
6. Acoustic stimuli for enhancing physiological functions (e.g., hearing, sleep)

Other non-medical applications for which EDA may be used to optimize a response include:
1. Navigational trajectories of vehicles (e.g., cars, planes, boats)
2. Monetary or other perturbations of economies
3. Fuel injection of combustible engines
4. Information transmission patterns in computer networks
5. Function of mechanical, electrical, and optical switches Extrema Distortion Algorithm: Harnessing Noise to Optimally Flip a Switch Stochastic search algorithms find optimal solutions without knowledge of the model. One of the major problems with stochastic search algorithms as it relates to time-varying signals is the "curse of dimensionality," that as we increase the resolution or duration of the optimal solution, the search space grows at an extremely rapid rate. While spike-triggered averaging avoids this problem, its relationship with optimality is more dependent on the solution space shape. Using spike-triggered averaging (STA), we may get close to optimality, but there would be no guarantee without knowing what the solution space looked like.

We now describe another method to use stochastic search, while minimizing the effect of the "curse of dimensionality." We address the curse of dimensionality by representing signals by their extrema points. Instead of searching neighboring solutions using every single point of the stimulus, we use the extrema as key features points. By distorting around these extrema, we can search for more optimal solutions using fewer dimensions.

We have tested this algorithm on three unique models: a Hodgkin-Huxley model for triggering a single action potential, a bistable FitzHugh-Nagumo model for suppressing repetitive firing, and a genetic toggle switch model for switching states. In each of these models, we have applied analytical techniques to compare the accuracy of the results from our algorithm.

Methods

Formalization of the Problem

We define the mechanics of our physiological system as $\dot{x}=f[x(t), u(t), t]$, where x(t) defines the m-dimensional states of the system and u(t) defines the n-dimensional stimulus. These definitions are generally the starting point from which traditional methods like calculus of variations or gradient-based algorithms solve for optimality. We focus our attention on the stimulus. Most implementations of stochastic algorithms treat each point in the stimulus as its own individual dimension. Thus, we can calculate the number of dimensions a stimulus requires by multiplying the duration of the stimulus by the resolution of the stimulus generator. Thus, if we have a 25-ms 1-dimensional stimulus generated at a 0.1-ms resolution, the solution space has a dimension of 250.

The fundamental concept underlying stochastic algorithms is that adaptive distortions of randomly generated initial estimates of solutions, which we designate as $u_0$, evolve towards an optimal solution, which we designate as $u_{optimal}$, based on some predefined criteria. We use the $L^2$-norm, or "energy" of the stimulus as the basis of our definition of optimality. We constrain our solution space to only solutions that successfully trigger a state change. Mathematically, our goal is to minimize $\int u^2 dt$ given that the solution exists in the solution space.

We modeled our algorithm initially off the stochastic hill-climbing approach in which a noise component, $\delta\mu$, is introduced to the original stimulus, allowing the algorithm to search locally for more optimal solutions. Once the algorithm finds a more optimal solution, that new solution, labeled, $\mu_1$, becomes the new starting point of yet another local search. Thus, this algorithm operates on the premise that $$\lim_{k \to \infty} \mu_k = \mu_{opt}$$

One of the observations we made early in our study was that with large dimensional solution spaces, the closer we were to optimality, the more dependent the dimensions became on each other. Thus, as we found solutions closer and closer to optimality, it was more important that both $\mu[t]$ and $\mu[t+1]$ moved in harmony. When these dimensional spaces are large, the probability of many different parameters moving in synchronization with each other became rarer, making it more difficult for the stochastic search to find more optimal solutions successfully.

Instead of focusing on manipulating every single data point in the stimulus, we focus on manipulating the extrema of each stimulus. This method has the benefit of allowing many degrees of freedom early in the process, but as the algorithm progresses, and extraneous extrema are removed, the degrees of freedom decreases, allowing for a higher probability of finding more optimal solutions.

In order to capture our starting seeds, we fed white noise stimuli into the system and captured only the snippets that successfully caused a state transition. These snippets became the starting seeds for our algorithm.

In order to validate our algorithm, we used the gradient algorithm as detailed in the parent application U.S. Ser. No. 62/139,014 to set up a benchmark by which we could compare our results.

Induction of an Action Potential: The Hodgkin Huxley Model

The Hodgkin-Huxley model is one of the best known computational models in biology. This model is a four dimensional system that captures the ionic mechanisms underlying the firing of an action potential in a single neuron. We apply our distortion algorithm to find the most energetically efficient, as defined by $L^2$-norm, stimulus that will cause a single neuron to fire an action potential. U.S. Ser. No. 62/139,014 U.S. Ser. No. 62/139,014 describes the mathematical model for the Hodgkin-Huxley neuron. Our goal for this model was to find the optimal 50-ms stimulus that would successfully cause the neuron to fire an action potential within 100-ms of the start of the stimulus.

For the Hodgkin-Huxley model, we multiplied the time intervals by a randomly generated number using a Gaussian distribution with mean of 1 and standard deviation of 0.25. We added to each peak a randomly generated number (Gaussian distribution with mean of 0 and standard deviation of 10% of the amplitude of the peak). We allowed the algorithm to run for 3,000 iterations.

Because we were looking for discrete state changes, a single action potential, we gave continuous white noise with an amplitude of 5 µA/cm$^2$ to the Hodgkin-Huxley model. Whenever an action potential occurred, we cut out the 50-ms snippet of stimulus proceeding the action potential. These snippets became the starting seeds of the Extrema Distortion Algorithm. We ran 10 seconds of white noise using a uniform distribution random number with a resolution of 0.1 ms, capturing 35 50-ms snippets.

Switching Off Oscillations: The Fitzhugh-Nagumo Model

The FitzHugh-Nagumo model of neuronal excitation is a two-dimensional model that has been used to abstractly describe a simple excitable neuron, as well as cardiac and circadian rhythms has been detailed in U.S. Ser. No. 62/139,014. The model is unitless, but regarding neuronal excitability, $x_1$ is analogous to Hodgkin-Huxley's V and m, while $x_2$ is analogous to Hodgkin-Huxley's h and n states. The variable u represents the current stimulation, which can be in the form of an endogenous persistent current or an exogenous input stimulus. Using the parameters found by Paydarfar and Buerkel, we defined a=0.7, b=0.8, c=3.0 and r=0.342. In this particular configuration, the system gravitates, when there is no stimulation, towards one of two states: quiescence (stable fixed point) or repetitive firing (stable oscillatory limit cycle). The minimum value of $x_1$ is the equivalent of the peak of an action potential in the FitzHugh-Nagumo model.

We are looking to minimize the energy needed to suppress repetitive firing, for instance in the clinical case of suppressing an epileptic neuron. We have previously determined the optimal shape and phase angle for the start of an 8-ms stimulus waveform. Thus, using the same parameters, we chose to apply the stimulus under the same starting conditions for the system ($x_1$=0.9302, $x_2$=−0.3760. Our goal for this model was to give an 8-ms stimulus, such that system suppresses repetitive firing stably for 92-ms after the stimulus is given.

We define suppression of repetitive firing as the lack of peaks less than −1.5 units tall, slightly smaller than the height of a normal action potential. For the FitzHugh-Nagumo model, we multiplied the time intervals by a randomly generated number using a Gaussian distribution with mean of 1 and standard deviation of 0.25. We added to each peak a randomly generated number with a Gaussian distribution with mean of 0 and standard deviation of 10% of the amplitude of the peak. We allowed the algorithm to run for 10,000 iterations.

The bistable system is slightly different from a monostable system in that it is a little harder to define a clear distinguishing feature that we could use to dictate what portion of the stimulus was contributing to the state change. As such, we gave discrete 8-ms snippets to the FitzHugh-Nagumo model and used successful snippets as the starting seeds for the Extrema Distortion Algorithm. We used white noise generated using a uniform distribution random number generator with an amplitude of 2 units and a resolution of 0.1 ms, capturing 49 snippets over the course of 1,000 total snippets.

As a proof of principle, we ran an instance of the Extrema Distortion Algorithm with 100-ms long stimulus. We wonder if the algorithm could guide us to knowing what the proper phase response of the stimulation should be. We were able to capture 16 100-ms white noise snippets that successfully suppressed repetitive firing.

Flipping a Genetic Toggle Switch

One of the more recent innovations in biotechnology has been the construction of genetic toggle switches. These switches play an important role in synthetic gene-regulatory networks by allowing transient stimuli, chemical, or thermal, to trigger state changes in bistable networks. This switch is composed of two repressors and two constitutive promoters. The opposing promoter, as seen in FIG. 2, transcribes each repressor.

FIG. 2 is a diagram of the genetic toggle switch, including Promoter 1, promoter 2, Repressor 1 and Repressor 2. FIG. 2 is adapted from Gardner T S, Cantor C R, Collins J J (2000) Construction of a genetic toggle switch in *Escherichia coli*. Nature 403: 339-342.

This model uses two state variables, u and v, representing the two repressor concentrations. The equations governing this system are:

$$\frac{du}{dt} = \frac{\alpha_1}{1+v^\beta} - u \qquad \frac{dv}{dt} = \frac{\alpha_2}{1+u^\gamma} - v$$

where $\alpha_1$ and $\alpha_2$ are the rate of synthesis of repressor 1 and repressor 2 respectively, $\beta$ is the cooperativity of repression of promoter 2 and $\gamma$ is the cooperativity of repression of promoter 1. They created a single plasmid that used the Lac repressor (lacI) in conjunction with the Ptrc-2 promoter as repressor 1 and a temperature-sensitive λ repressor (cIts), in conjunction with a $P_L$s1con promoter as repressor 2.

Because of this particular setup, the parameters of the model are $\alpha_1=156.25$, $\alpha_2=15.6$, $\beta=2.5$, and $\gamma=1$.

In this toggle switch, only one of the concentrations is elevated at any given time. They used a pulse of isopropyl-β-D-thiogalactopyranoside (IPTG) to switch the system so that the lad concentration was elevated, and then used a thermal pulse to switch the system back. The model was expanded to include IPTG as the exogenous stimulus to the system.

$$\frac{dv}{dt} = \frac{\alpha_2}{1+\left(\frac{u}{\left(1+\frac{[IPTG]}{K}\right)^\eta}\right)^\gamma} - v$$

where K is the dissociation constant of IPTG from LacR and is the cooperativity of IPTG binding. K is set at $2.9618 \times 10^{-5}$, and $\eta=2.0015$. Using the model, we can calculate the stable points by setting $$\frac{du}{dt} \text{ and } \frac{dv}{dt}$$

to zero. We learn that there are two stable fixed points: (0.3319, 11.7080) and (155.5143, 0.0995). An unstable fixed point was calculated at (1.3144, 6.7342).

From the literature, we have seen that a 20-minute pulse of IPTG is used to constitutively turn on lad protein production. Our goal was to find the optimal 20-minute pulse of IPTG that would turn off the lad protein production at the end of 20 minutes. One of the twists regarding the genetic toggle switch model is that the stimuli need to be positive-only because the stimulus represents the concentration of IPTG. A negative concentration is impossible. Thus, when finding our starting snippets, we tested 20-minute discrete non-negative intensity snippets. We generated white noise using a uniform distribution random number generate with an amplitude of 0.0002 and a resolution of 0.1 minutes, capturing 29 snippets out of 50 snippets. In the distortion phase, instead of adding a randomly generated number to the peak, we multiplied the peak by a randomly generated number with a Gaussian distribution with mean of 1 and standard deviation of 0.1. This way, the values would stay positive. For the genetic toggle switch model, we multiplied the time intervals by a randomly generated number with a Gaussian distribution with mean of 1 and standard deviation of 0.25. The algorithm iterations 2,000 times.

Results

We applied the Extrema Distortion Algorithm to three unique models to display the adaptability of this algorithm to a range of different systems. We have chosen two of the classic computational models used in neuroscience: the Hodgkin-Huxley model for triggering a single action potential, and the FitzHugh-Nagumo model for suppressing repetitive firing. We have also chosen to apply this algorithm to a relatively new model in synthetic biology, the genetic toggle switch for causing a switch from one state to the other.

Induction of an Action Potential: The Hodgkin Huxley Model

We ran 35 instances of the Extrema Distortion Algorithm, each with a unique starting seed. FIG. 3A through FIG. 3H illustrate the path the algorithm takes as it begins with a stochastically generated initial stimulus, and it slowly evolves towards the optimal stimuli.

FIG. 3A through FIG. 3H illustrate the progression of waveforms that occur in applying the Extrema Distortion Algorithm. As illustrated in FIG. 3A through 3H, the Extrema Distortion Algorithm shapes stochastically generated stimuli towards an optimal waveform. FIG. 3A through 3H illustrate the progression of solutions from the original white noise stimulus in the 1st iteration to the 2nd, 5th, 10th, 20th, 50th, 1000th and 5000th iteration, respectively. By convention, positive current is depolarizing.

The algorithm makes substantial improvements even within the first 10 iterations, when fundamental shapes become visible. By 50 iterations, most of the noise disappeared, and we saw convergence to a solution at 5,000 iterations.

Because this is an Extrema Distortion Algorithm, we can monitor the extrema time and amplitude over the course of the algorithm as well as seen in FIG. 4A and FIG. 4B.

FIG. 4A and FIG. 4B and diagrams that illustrate how the extrema in the signal evolve over the course of the algorithm.

FIG. 4A is a diagram that shows the timing of the extrema as a function of iteration number.

FIG. 4B is a diagram that shows the amplitude of the extrema as a function of iteration number.

Both the timing and the amplitude of the extrema begin randomly scattered. Over the course of a few iterations, it rapidly converges towards a few key locations. Over the course of a few hundred iterations, one can see the algorithm prune away at unnecessary extrema.

Here we can see that again, the algorithm begins with stochastically generated stimuli where the extrema are uniformly scattered out both in time and amplitude. Over the course of 100 iterations, we can see the algorithm pruning away extraneous extrema, converging the remaining extrema towards specific locations. There is a brief moment around 900 iterations where the algorithm does not find any improvement for a short period, but then it is able to find an improvement, which leads to more optimal solutions.

The resulting 35 stimuli had an average $L^2$-norm of 15.550 and a standard deviation of 0.149.

FIG. 5A is a diagram that shows the progression of improvement in stimulus energy over the 5,000 iterations for 35 snippets.

FIG. 5B is a diagram that shows the resulting stimuli for all 35 snippets.

The algorithm takes randomly generated stimuli and evolves them towards a single global optimal solution for the Hodgkin-Huxley model. As seen from the time course of the stimulus energy (FIG. 5A), the algorithm begins with very energetic stochastically generated stimuli and rapidly finds more energetically efficient stimuli. FIG. 5B shows all of the resulting stimuli overlaid on top of each other, aligned by where they cause an action potential to occur. The stimulus' baseline is at 0 μA/cm²

We lined up the resulting 35 stimuli based on where the action potential occurred. As we can see, the algorithm did a good job at converging the various stochastically generated noise samples towards the optimal solutions.

The best of the 35 snippets had an $L^2$-norm of 15.270 compared to what we were able to determined using the gradient algorithm, 15.354.

FIG. 6A is a graph that shows a result from the best of the 35 snippets using distortion of the extrema (curve 620) as compared to the best of the 35 snippets using distortion of all the points (curve 610).

While the fundamental shape is very similar, the result using distortion of all the points retains more noise than the result using distortion of only the extrema.

FIG. 6B is a graph that shows the range of stimulus energy in 35 runs of both the Extrema Distortion Algorithm as well as the gradient algorithm. The stimulus' baseline is at 0 µA/cm$^2$.

FIG. 6A shows the comparison of the best result from the distortion algorithm compared to the result from the gradient algorithm. While we do see that the best of the Extrema Distortion Algorithm is better than the result from the gradient algorithm, we found that the variation among the 35 resulting snippets were much larger using the Extrema Distortion Algorithm compared to the gradient algorithm, as seen in FIG. 6B.

The choice to use extrema instead of every single data point was to combat the "curse of dimensionality." We hypothesized that using the extrema alone would improve computational efficiency of the algorithm as well as produce results that are more accurate. In order to test this hypothesis, we reconfigured our algorithm to use every single data point in what we are calling the all-points distortion algorithm instead of the Extrema Distortion Algorithm. As we can see in FIG. 7A and FIG. 7B, the improvement of $L^2$-norm across the 35 snippets using Extrema Distortion Algorithm converges towards an optimal solution faster than the improvement of $L^2$-norm across 35 snippets using the all-points distortion algorithm.

Figures 7A, 7B:
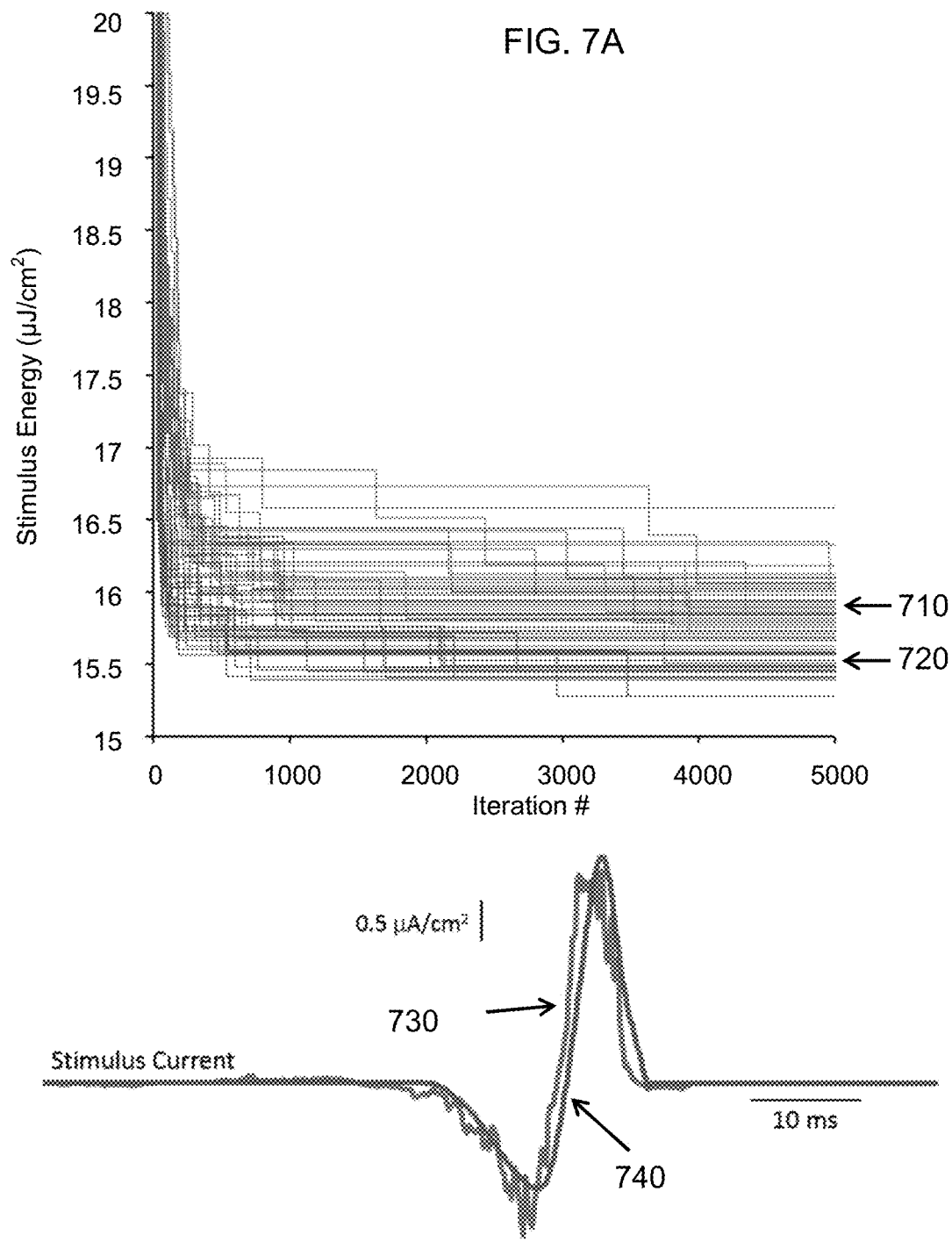
FIG. 7A is a graph which shows that the Extrema Distortion Algorithm (curve 720) finds solutions more efficiently than an all-points distortion algorithm (curve 710). We show both the $L^2$-norm progress of 5,000 iterations across both algorithms for the same initial 35 snippets in panel A.
FIG. 7B showing is a graph the best solution from both algorithms. The Extrema Distortion Algorithm solution (curve 740) and the all-points distortion algorithm solution (curve 730) are illustrated. The stimulus' baseline is at 0 $\mu A/cm^2$.

FIG. 7A is a graph which shows that the Extrema Distortion Algorithm (curve 720) finds solutions more efficiently than an all-points distortion algorithm (curve 710). We show both the $L^2$-norm progress of 5,000 iterations across both algorithms for the same initial 35 snippets in panel A.

FIG. 7B showing is a graph the best solution from both algorithms. The Extrema Distortion Algorithm solution (curve 740) and the all-points distortion algorithm solution (curve 730) are illustrated. The stimulus' baseline is at 0 µA/cm$^2$.

Quantitatively, the average $L^2$-norm of the all-points distortion algorithm is 15.902 with a standard deviation of 0.171. The best result from all-points distortion algorithm has an $L^2$-norm of 15.683. FIG. 7B shows that the best result in all-points distortion retains a considerable level of noise as compared to the best result in extrema distortion. Both of these results support our hypothesis that the extrema distortion is more efficient than the all-points distortion method, while maintaining a high level of accuracy.

Switching Off Oscillations: The Fitzhugh-Nagumo Model

To push the algorithm further, we applied the algorithm to a bistable FitzHugh-Nagumo model to see how the algorithm would perform when suppressing repetitive firing in a bistable system. We captured 49 white noise snippets, which we then ran through the Extrema Distortion Algorithm. We noted that the resulting stimuli fell into one of two modes: one mode with an average $L^2$-norm of 0.504 and a standard deviation of 0.079, while the other mode had an average $L^2$-norm of 7.207×10$^{-4}$ and a standard deviation of 2.778× 10$^4$. FIG. 8A through FIG. 8C show the final form of all 49 stimuli separated into the two modes. FIG. 8A is a graph showing that the Extrema Distortion Algorithm converges towards the two locally optimal solutions in the FitzHugh-Nagumo model, with the model response curves 810 corresponding to the stimuli shown in FIG. 8B and the response curves 820 corresponding to the stimuli shown in FIG. 8C.

FIG. 8B is a graph of a first set of stimuli.

FIG. 8C is a graph of a second set of stimuli, which are much smaller in scale than the stimuli shown in FIG. 8B. The snippets are aligned such that the first valley after repetitive firing has ended occurs at 0 ms. The stimulus' baseline is at zero.

These waveforms correspond to results that we have obtained from the gradient algorithm, which produced two separate shapes, the smaller one with an $L^2$-norm of 0.0112 while the larger one had an $L^2$-norm of 1.1277.

We observed that the Extrema Distortion Algorithm performs better than the gradient algorithm in both shapes. Upon closer examination, we realize that this was because we had different definitions of successful transition between the two algorithms. The Extrema Distortion Algorithm was set to find an optimal solution that suppressed action potentials, while the gradient algorithm was find an optimal solution that suppressed all oscillatory activity. Because the FitzHugh-Nagumo quiescent state has a shallow basin of convergence, the state can oscillate at a sub-action potential level for a longer period before arriving at the fixed point. Thus, simply suppressing action potentials does not necessarily equate to arriving at the fixed point.

In order to account for this difference between the two algorithms, we applied stricter definitions of success to the Extrema Distortion Algorithm. Because we were unable to find any stimuli that took the system exactly to the fixed point of quiescence, we were unable to use that as the exact criteria. What we did instead was shrink the definition of success in different experiments until we were no longer able to find any successful white-noise solutions to use as starting seeds.

The resulting stimuli using a much tighter definition of success again was bimodal with the smaller set having an average $L^2$-norm of 0.0072 and a standard deviation of 0.0018, while the larger set had a an average of 1.094 and a standard deviation of 0.123. FIG. 9A through FIG. 9C show just the smaller set of solutions found and compares the result from the gradient algorithm to the results from both the loose and strict definitions of successful transitions.

FIG. 9A is a graph showing stimuli that result from the gradient algorithm (curve 910) as well as two versions of the Extrema Distortion Algorithm. The first version of the Extrema Distortion Algorithm (curve 920) limits the terminal condition of success to be extremely close to the fixed point similar to the gradient algorithm. The second version of the Extrema Distortion Algorithm (curve 930) specifies the condition of success to just be a suppression of action potentials ($-x_1<1.5$).

FIG. 9B shows the state space of the system's response to the various stimuli. The stimulus's baseline is at 0.

FIG. 9C shows an expanded view of a region shown in FIG. 9B next to the fixed point 940. Curves 950, 960 and 970 are the responses to stimuli 910, 920 and 930, respectively.

The Extrema Distortion Algorithm allows for more flexibility in terminal conditions leading to more optimal results. As seen here, the stricter definition of successful transitions does indeed find a waveform closer in shape to the solution found using the gradient algorithm.

Finally, we examine how robust the Extrema Distortion Algorithm works with long stimulus durations. The purpose of this experiment was two-fold. First, we wanted to test the robustness of the Extrema Distortion Algorithm when using large dimensional stimuli. Secondly, from a clinical perspective, the optimal phase and stimulus duration are often unknowns. We wanted to find out if our algorithm could assist in the determination of these parameters by allowing it a great deal of flexibility to find optimal solutions. FIG.

10A and FIG. 10B show the results from 17 white-noise snippets, aligned by where the first sub-action potential peak occurs after the transition from repetitive firing to quiescence.

FIG. 10A is a graph showing a response of the FitzHugh-Nagumo model. The Extrema Distortion Algorithm can be used to gain insight into the phase-dependency and duration of the optimal stimulus. The Extrema Distortion Algorithm used on 17 unique 100-ms snippets shows converge towards a phase-specific stimulus waveform. These snippets were all aligned such that the first peak after the action potential occurred at 100 ms.

FIG. 10B is a graph of the stimulus that generated the response shown in FIG. 10A. The stimulus's baseline is at 0.

As we can see, the algorithm does give general structures for what the shape of the optimal stimulus should be, as well as phase information. From what we can see in FIG. 109A, the optimal stimulus waveform is in anti-phase to the system response in order to cause successful transition from repetitive firing to quiescence. As seen in FIG. 10B, when we overlay all the solutions on top of each other, there is a remarkable amount of convergence between them.

Flipping a Genetic Toggle Switch

So far, our applications have been neurologically based, but this algorithm is completely model agnostic. Thus, we decided to expand our test cases to a non-neurological model. The genetic toggle switch, a relatively recent development in synthetic biology, is a bistable system, but instead of having one oscillatory state and one fixed state like the FitzHugh-Nagumo, both stable states are fixed. We ran 29 white-noise snippets through the Extrema Distortion Algorithm. The resulting optimal stimuli had an average $L^2$-norm of $2.968 \times 10^{-8}$ and a standard deviation of $2.25 \times 10^{-9}$.

FIG. 11A is a graph of a stimulus in terms of concentration of [IPTG] as a function of time for the Extrema Distortion Algorithm (curve 1110) and for the gradient algorithm (curve 1120). The stimulus starts at 0 M [IPTG].

FIG. 11B is a graph of the concentration of Repressor 2, [Repressor 2] as a function of time for the Extrema Distortion Algorithm (curve 1130) and for the gradient algorithm (curve 1140). The algorithms produce very similar waveforms. Success is defined by seeing a transition occur at 20 minutes.

FIG. 11C is a graph of a stimulus in terms of concentration of [IPTG] as a function of time for the Extrema Distortion Algorithm (curve 1150) and for the gradient algorithm (curve 1160), The stimulus starts at 0 M [IPTG].

FIG. 11D is a graph of the concentration of Repressor 2, [Repressor 2] as a function of time for the Extrema Distortion Algorithm (curve 1170) and for the gradient algorithm (curve 1180). The algorithms produce very similar waveforms. Success defines the transition occurring at 100 minutes, while the stimulus duration is still kept at 20 minutes. The gradient algorithm calculates the optimal stimulus using knowledge of where the separatrix, while the Extrema Distortion Algorithm does not.

FIG. 11A through FIG. 11D show the best of the 29, with an $L^2$-norm of $2.563 \times 10^{-8}$, along with the results from the gradient algorithm, which has an $L^2$-norm of $2.487 \times 10^{-8}$. Again, we can see that the two results are similar in both shape as well as $L^2$-norm value.

As we had seen with the FitzHugh-Nagumo model, a change in the definition of success could result in a different optimal solution. In searching for the optimal stimuli, we wanted the system to reach the terminal state at the end of the 20 minutes. For practical implementation, one may only need it to have switched from being in the basin of attraction of one state to being in the basin of attraction of the other state. In this desired implementation, one would only need to find an optimal stimulus that would cross the separatrix instead of travel all the way over to the other state. Thus, we reconfigured the gradient algorithm to find the optimal stimuli to the separatrix. We ran our Extrema Distortion Algorithm with a 20-minute stimulus, but instead of setting the condition of success as reaching the terminal state by the end of 20 minutes, we set it to reach the terminal state by 100 minutes. With the gradient algorithm, we had a mathematical model that we could use to calculate where the separatrix existed. Because we wanted to maintain our model-independent principle, we allowed the algorithm to reach the terminal condition at a more distant point in time, meaning that the stimulus must have cleared the separatrix in the first 20 minutes in order for it to transition. FIG. 11C and FIG. 11D show one of the results we found compared to the gradient algorithm. Again, we can see that the Extrema Distortion Algorithm was able to find a solution that had a very similar waveform shape and $L^2$-norm values as the gradient algorithm. It is interesting to see that the Extrema Distortion Algorithm was able to evolve a solution that learned where the separatrix existed even without any knowledge of the mathematical model underlying the system.

Figure 12:
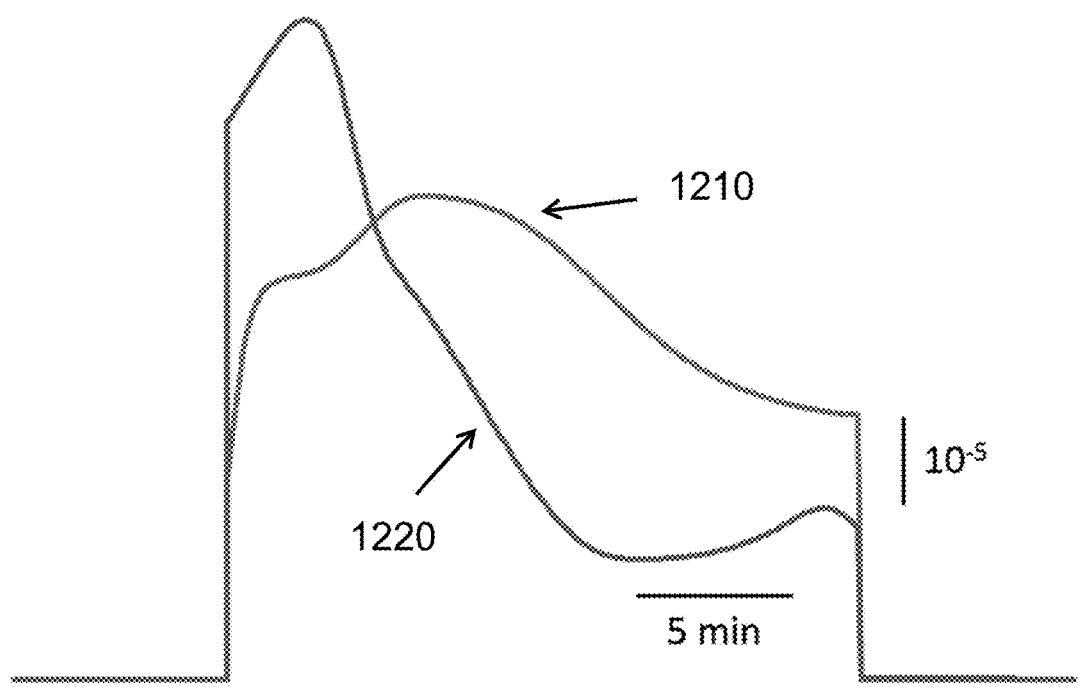
FIG. 12 is a graph showing the optimal stimuli discovered by the Extrema Distortion Algorithm using the $L^2$-norm performance metric (curve 1210) and the maximum amplitude performance metric (curve 1220). The stimulus starts at 0 M [IPTG]. The Extrema Distortion Algorithm can discover optimal stimuli based on different performance metrics.

So far, we have been doing all our analysis using the $L^2$-norm as an indicator of performance. When dealing with chemical reactions however, the $L^2$-norm has very little qualitative meaning. In most chemical reactions, it is more important to minimize the maximum dosage of the stimulus at any given time. We ran the Extrema Distortion Algorithm again using our goal as peak minimization. FIG. 12 is a graph showing the optimal stimuli discovered by the Extrema Distortion Algorithm using the $L^2$-norm performance metric (curve 1210) and the maximum amplitude performance metric (curve 1220). The stimulus starts at 0 M [IPTG]. The Extrema Distortion Algorithm can discover optimal stimuli based on different performance metrics.

Evaluating the Use of Pre-Processing Noise Filter

In the course of this work, we speculated that some initial filter of the seed would be useful to increase the efficiency of the algorithm. As such, we explored this idea by using Empirical Mode Decomposition (EMD) to break down the successful white noise snippets into what we termed "distilled" snippets. We then processed these distilled snippets through the Extrema Distortion Algorithm, allowing us to evaluate the benefits of the noise filter.

Pure white noise snippets contain many extrema. We hypothesized that if we were able to reduce the number of extrema down to just the right number of extrema, each iteration of the distortion algorithm would require fewer computations, and thus over all the algorithm would be more efficient. In order to distill the snippets down, we considered using Fourier analysis, wavelet analysis, and EMD to break down the white noise snippets, determining the fundamental component of the snippet causing the state transition. We decided to use the Empirical Mode Decomposition. Because we were working with short discrete stimuli, we did not want to use Fourier analysis because of the known edge effects. Furthermore, we chose not to use wavelet analysis because we were concerned that the choice of wavelets may bias the results.

Thus, we chose to use EMD to separate out the white noise snippets into a set of intrinsic mode functions (IMFs). We tested every combination of consecutive IMFs, scaling each combination until it just barely caused a state transition.

From these results, we chose the combination of consecutive IMFs that used the least amount of energy.

The distillation process is able to reduce many of the white noise snippets into very energy efficient snippets that successfully cause a state transition with a mean $L^2$-norm of 29.206 and standard deviation of 8.256. We used these resulting filtered snippets as the starting seeds of the Extrema Distortion Algorithm. The resulting distilled and distorted snippets have a mean $L^2$-norm of 16.695 and standard deviation of 1.3194.

Figure 13:
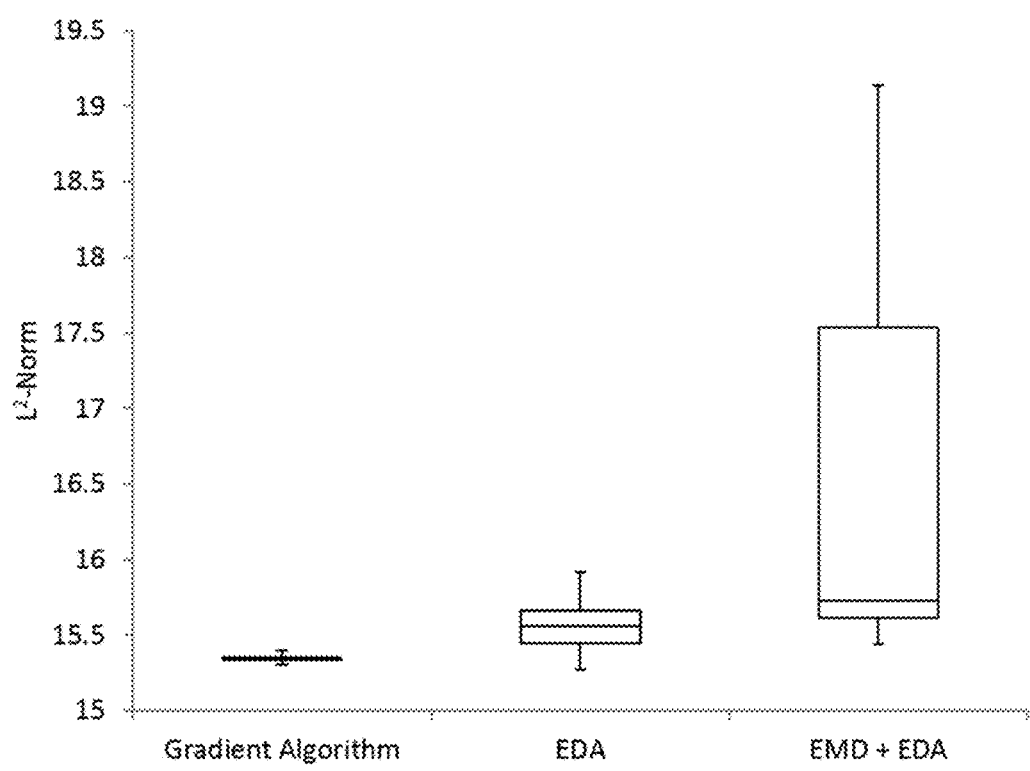
FIG. 13 is a bar graph showing a comparison of the ranges of $L^2$-norm results between the gradient algorithm, the Extrema Distortion Algorithm, and the Empirical Mode Decomposition combined with the Extrema Distortion Algorithm.

FIG. 13 is a bar graph showing a comparison of the ranges of $L^2$-norm results between the gradient algorithm, the Extrema Distortion Algorithm, and the Empirical Mode Decomposition combined with the Extrema Distortion Algorithm.

Figure 14:
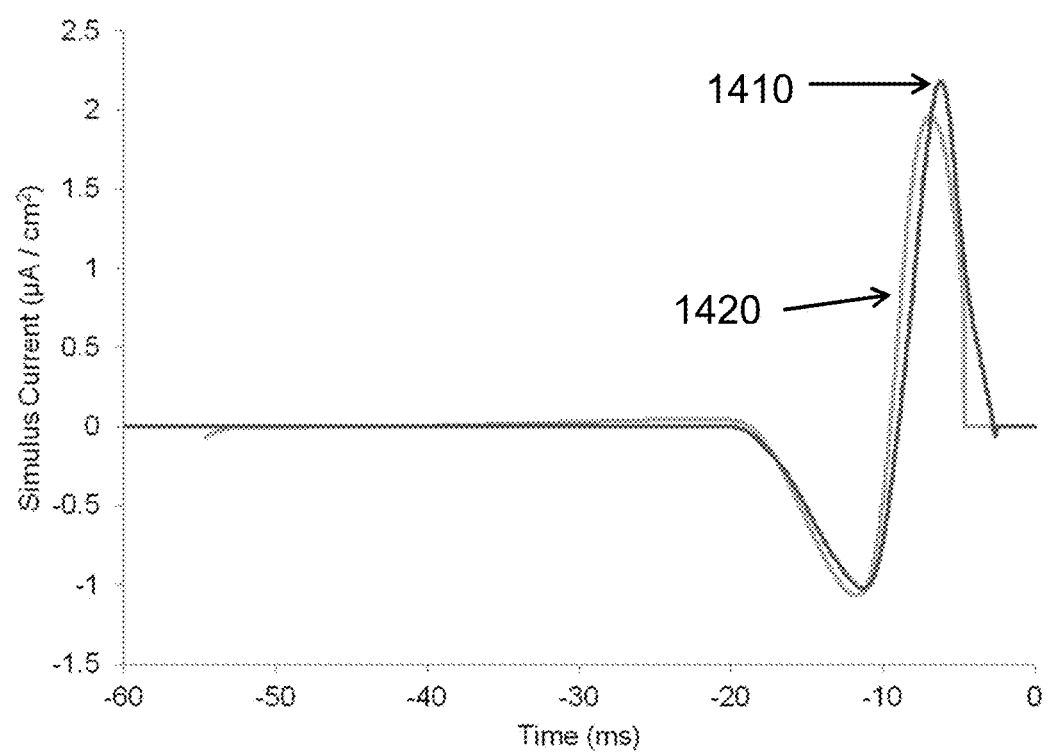
FIG. 14 is a graph showing a comparison of the best result from Extrema Distortion Algorithm (curve 1410) with the best result from the Extrema Distortion Algorithm combined with an initial Empirical Mode Decomposition denoising (curve 1420). The stimulus is aligned such that the action potential occurs at 0 ms.

FIG. 13 shows that compared to just during extrema distortion alone with no filtering (mean=15.550, standard deviation=0.149), running EMD before EDA caused increased variability. The best result from doing the pre-processing had an $L^2$-norm of 15.438, which was comparable to the 15.275 from the Extrema Distortion Algorithm alone. FIG. 14 is a graph showing a comparison of the best result from Extrema Distortion Algorithm (curve 1410) with the best result from the Extrema Distortion Algorithm combined with an initial Empirical Mode Decomposition denoising (curve 1420), e.g., with and without pre-processing filter. The stimulus is aligned such that the action potential occurs at 0 ms.

There is no correlation between how well a snippet did after the distillation phase as compared to the distortion phase. Furthermore, it would seem that the distillation process produced solutions that were worse than those generated from using only distortion were. Our conclusion is that it is possible for any sort of pre-processing work to oversimplify the white noise snippets, biasing the signal away from optimality. Future research and algorithm development may show how better to reduce the amount of noise to start from the white noise snippet, while not biasing the solution.

As can be seen in our results, the Extrema Distortion Algorithm is able to find stimulus waveforms that are very close to what we have analytically calculated to be optimal. The use of extrema in simplifying data sets is not a novel concept in the field of signal processing. In the field of pattern recognition, certain algorithms use the coordinates of robust extrema to simplify the number of points to match. In computer vision, extrema are used as key feature markers for object recognition and multi-scale representation of the original images. In many of these algorithms, extrema mark key feature points, and thus, they construct a simplified representation of the original signal retaining only the most important components. This makes the manipulation and usage of the signals more efficient and simpler.

To our knowledge, algorithms that search for optimal stimulus waveforms have not used extrema. As we have stated, one of the biggest problems with searching for optimal stimulus waveforms is that they exist in a very high dimensional solution space. Some researchers approach this problem head on and apply search algorithms to the entire solution space, but others choose to simplify the solution space by making certain assumptions. One of the most common methods of simplifying the solution space is by assuming certain basic shapes. For instance, a number of studies search for the optimal dimensions of rectangular pulses for causing state transitions. One study recently tried using the pivot points of cubic splines to redefine and simplify the solution space. The problem with most of these studies that seek to simplify the solution space is that they bring in certain presuppositions of what the optimal stimulus waveform looks like. Studies have shown that the rectangular pulse is not energetically efficient, and thus the use of these simplifications limit the possibilities of even better optimal stimulus shapes.

One of the benefits of the Extrema Distortion Algorithm is that there are no presuppositions about optimality introduced into the algorithm. The algorithm begins with stochastically generated noise containing many extrema. This is beneficial in that it allows the stimulus to have more degrees of freedom to explore for optimality at the beginning when the algorithm knows little about the optimal solution. As the algorithm progresses, unnecessary extrema are filtered out, increasing the efficiency of the algorithm.

One weakness with the algorithm is that we assume a linear transformation from one set of extrema to the other. Once the waveform shape has been determined between extrema, there is little chance that it will change again. So far, in the three examples we have used, we have not noticed this to be a problem. We postulate that because we are beginning with many extrema, each extrema has the opportunity to be at the proper inflection points in the waveform before they disappear. To improve this technique in the future, we may want to examine methods to aid in the search and verification of intermediate points as well as the extrema.

In the Hodgkin-Huxley model, we noticed that the best result from the Extrema Distortion Algorithm produced an even better result than that found using the gradient algorithm. While this surprised us at first, we realized that this result showed us the limitations of the gradient algorithm. We used a first-order gradient algorithm for its robustness to initial conditions. However, a first-order gradient algorithm has the weakness of not being able to fine-tune convergence when it sits very close to optimality because it overestimates or underestimates the next step due to its use of only first-order gradients. Many algorithms need to trade between the ability to converge towards optimality and robustness to initial conditions. The fact that the Extrema Distortion Algorithm can at times surpass analytical methods is thus a pleasant surprise. That being said, it is important to realize that while the best of the Extrema Distortion Algorithm was able to successfully find a better solution, there were many solutions found that although were close, were not as good as the gradient algorithm. This variability is an inherent component of any stochastic algorithm.

While this algorithm has performed both accurately and efficiently, it is a rather simplistic algorithm in the world of model-independent optimization techniques. By examining these other techniques, we can gain ideas on how to improve both the accuracy and the efficiency of this algorithm. We highlight at least three areas that we think future research may explore using our algorithm as a first step: initial noise filtration, cross learning between different seeds, and incorporation of statistical principles to guide choice of next stimulus.

One of the first things we noticed when developing this algorithm is that there is an excessive level of noise in the starting seeds. We speculate that if we were able to remove this noise, we would be able to converge quicker towards the optimal solution. We describe later our first attempt to filter out some of the noise. Unfortunately, we have found that while filtering can help reduce the noise, how well a stimulus does after filtering does not necessarily correlate to how well it will do after the distortion process. Furthermore, sometimes filtering the stimulus can bias it towards a specific waveform shape and thus push the solution further away from optimality as opposed to towards optimality.

Secondly, we recognize that the Extrema Distortion Algorithm utilizes at its heart a stochastic hill-climbing approach, which starts with a single seed and progresses its way forward without any input from how other parallel processes are performing. As we have stated before, stochastic hill-climbing is one of the simplest approaches. More recently, there has been growing interest in population-based evolutionary algorithms like genetic algorithms and particle swarm optimization. These algorithms incorporate a learning process between different runs of the algorithm that start with different seeds. One of the earlier studies that looked at model-free methods to obtaining optimal stimulus waveforms used genetic algorithms. Unfortunately, most of these population-based algorithms require all the solutions share a common dimensionality in order for them to be able to recombine. Our algorithm does not meet that criterion as the number of extrema changes from one solution to the next. However, the concept of allowing some form of learning between solutions is an area for future investigation as we may be able to boost efficiency of the algorithm.

Finally, the algorithm chooses the next stimulus by examining a set of randomly chosen neighboring stimuli with no guidance as to where better solutions may come from. The algorithm samples all neighboring solutions with equal probability. One interesting approach that we came across when examining optimal stimulus waveforms was efficient global optimization (EGO), which constructs a generalized least squares model of the response surface by making the assumption that solutions close together will elicit similar responses from the system in question. The algorithm tests a set of points in the solution space in such a way as to minimize the error potential of the response surface model by choosing new points to test that have the highest level of uncertainty as determined through statistical means.

Unfortunately, this method assumes a continuous response surface. In our search for optimal stimulus waveforms, we need to take into account the fact that certain stimuli do not successfully cause the state change that we want. We break the assumption that neighboring solutions have similar responses due to solutions that sit close to the boundary between successful and unsuccessful stimuli. While EGO may not directly be applicable, the concept of incorporating some sort of statistical measurement to guide the algorithm in sampling neighboring solutions is an area of future research that could improve the efficiency of the algorithm further.

What we have done in this study is present a first step in the development of a stochastic optimization algorithm for black-box systems to find optimal stimulation for physiological systems that utilizes extrema to simplify the search space. With further development by potentially incorporating noise filters, learning mechanisms or statistical principles, we may see these algorithms applied in a clinical setting to determine efficiently optimal stimulus waveforms for therapeutic treatments.

Optimally Suppressing Epileptic Seizures

Epilepsy affects 2.3 million adults and over 450,000 children under the age of 18 in the United States. Physicians diagnose roughly 150,000 new cases each year. The total financial burden of this disease in both direct and indirect costs was estimated at $9.6 billion in 2009. While the primary form of treatment for epilepsy is in the form of anti-seizure medication, nearly 30% of these patients do not respond to drug therapies. While some patients can undergo surgery to treat refractory epilepsy, not all medically refractory patients are candidates for these procedures. As an alternative, it has been shown that electrical stimulation of specific regions of the brain can aid in the suppression of seizure frequency and severity.

One of the key features of epileptic seizures is dysfunctional neurological oscillatory activity. Treatment for epilepsy via electrical stimuli has focused on the rectification or suppression of these dysfunctional oscillations. To that end, three different types of treatments have been developed: vagus nerve stimulation, deep brain stimulation of the thalamus, the subthalamic nucleus, the caudate nucleus and the cerebellum, and responsive neural stimulation of cortical epileptogenic regions. In each of these treatments, a fundamental waveform is used, and physicians tweak a few basic parameters including frequency, pulse duration, and amplitude based on how the patient responds in order to improve performance.

An important computational challenge arises here not only to find stimuli that successfully suppress seizures, but also to minimize its energy usage. Each of the existing treatments has some adverse effects potentially related to energy leakage from the stimuli into neighboring areas. For instance, patients that are given vagal nerve stimuli have demonstrated coughing, voice alteration, paraesthesia, dyspnea and headache. Patients undergoing deep brain stimulation appear to be less prone to adverse effects, but there have been reports of depression, memory impairment, anxiety, and paraesthesia related to stimulation. Patients undergoing responsive neural stimulation of the cortex have shown instances of implant site pain, headaches, and dysesthesia.

We apply the Extrema Distortion Algorithm to four separate mathematical models of epilepsy based on different mechanisms examining different levels of complexity. We demonstrated how this algorithm is able to find optimal solutions relatively quickly without any bias towards one waveform over another and without needing any knowledge of the mechanisms underlying the models. By applying this algorithm to the four separate models, we seek to gain therapeutic insights into the clinical treatment of epilepsy with electrical stimulation.

Methods

Extrema Distortion Algorithm

The Extrema Distortion Algorithm (EDA) finds optimal stimulus waveforms without requiring any a priori knowledge of the underlying mechanisms or mathematical equations defining the system or behavior. EDA works by iteratively taking a starting waveform and allowing its extrema (the peaks and valleys) of the stimulus, to move around in search for a more optimal stimulus. This more optimal stimulus becomes the starting waveform for the next iteration.

We first seed the algorithm by applying white noise into the model in search for snippets that successfully cause the desired outcome. The white noise snippets that successfully trigger the outcome turn into the seeds for EDA. In all of the experiments done in this study, we sought to minimize the energy usage of the stimulus as conventionally defined by the $L^2$-norm, which is the sum of the squares of the stimulus amplitudes over time.

Devices giving electrical charge to the body attempt to do so in such a way that the net electrical charge injected is equal to zero. This is because if excessive charge builds up in the body, irreversible damage is done to the neural tissue. As such, we added a new constraint to our algorithm such that after every distortion, we subtract the mean of the stimulus from the stimulus. This forces each distortion to produce only zero-mean stimulus waveforms. Thus, we were able to restrict the search space for all the experiments to return only charge-neutral solutions. We ran each experiment twenty times with different starting seeds each time.

Single Cell Repetitive Firing

In many instances of epilepsy, seizure activity arises from a derangement in the neuron's intrinsic properties resulting in repetitive firing. A subset of epilepsies falls in the category of channelopathies, mutations in genes that encode various ionic channels. Among these channelopathies, forms of generalized epilepsy with febrile seizures has been linked to mutations in genes encoding voltage-gated sodium channel α, leading to persistent inward current which likely causes increased excitability of the neuron's membrane. To model this, we have added a 9 μA/cm² persistent current to the Hodgkin-Huxley model, essentially increasing the excitability of the neuron's membrane. Our model consists of the following equations:

$$C\dot{V} = 120m^3h(V-115) - 36n^4(V+12) - 0.3(V-10.613) - 9 - u \quad (1)$$

$$\dot{m} = -m(\alpha_m(V) + \beta_m(V)) + \alpha_m(V) \quad (2)$$

$$\dot{n} = -n(\alpha_n(V) + \beta_n(V)) + \alpha_n(V) \quad (3)$$

$$\dot{h} = -h(\alpha_h(V) + \beta_h(V)) + \alpha_h(V) \quad (4)$$

$$\alpha_m(V) = \frac{0.1\phi(25-V)}{e^{0.1(25-V)}-1},\ \beta_m(V) = 4\phi e^{-V/80} \quad (5)$$

$$\alpha_n(V) = \frac{0.01\phi(10-V)}{e^{0.1(10-V)}-1},\ \beta_n(V) = 0.125\phi e^{-V/80} \quad (6)$$

$$\alpha_h(V) = 0.07\phi e^{-V/20},\ \beta_m(V) = \frac{\phi}{e^{0.1(30-V)}+1} \quad (7)$$

where V is the membrane voltage, m, n, and h represent dimensionless quantities associated with sodium channel activation, potassium channel activation, and sodium channel inactivation respectively, and u represents the exogenous stimulation we are looking to input into the system. The addition of the persistent current causes the Hodgkin-Huxley model that we have defined here to be bistable representing the increased excitability found in cells prone to seizures.

Using EDA, we found the optimal 31-ms stimulus (the duration of two cycles of repetitive firing) that successfully suppressed the system from repetitive firing to quiescence where the membrane voltage no longer went above 50 mV.

Single Cell Bursting

There has been recent work that has examined the possibility that the epileptic cell is not repetitively firing, but instead bursting (e.g. firing sets of action potentials followed by temporary quiescence). Cressman et al. have worked to develop a more accurate model of a single-cell neuron that includes the interaction of the neuron with the different ionic concentrations in its microenvironment in an attempt to model this bursting behavior.

The equations for this model are as follows:

$$C\dot{V} = I_{Na} + I_K + I_{Cl} \quad (12)$$

$$I_{Na} = -g_{Na}[m_\infty(V)]^3 h(V - V_{Na}) - g_{NaL}(V - V_{Na}) \quad (13)$$

$$I_K = -\left(g_K n^4 + \frac{g_{AHP}[Ca]_i}{1+[Ca]_i}\right)(V - V_K) - g_{KL}(V - V_K) \quad (14)$$

-continued $$I_{Cl} = -g_{ClL}(V - V_{Cl}) \quad (15)$$

$$\dot{q} = \phi[\alpha_q(V)(1-q) - \beta_q(V)q],\ \text{where}\ q = n, h \quad (16)$$

$$[\dot{C}a]_i = \frac{-0.002 g_{Ca}(V - V_{Ca})}{1 + e^{\frac{V+25}{2.5}}} - \frac{[Ca]_i}{80} \quad (17)$$

$$[\dot{K}]_o = -0.33I_K - 2\beta I_{pump} - I_{glia} - I_{diff} \quad (18)$$

$$[\dot{N}a]_i = 0.33\frac{I_{Na}}{\beta} - 3I_{pump} \quad (19)$$

Variables and accessory equations are detailed in Cressman J R, Ullah G, Ziburkus J, Schiff S J, Barreto E. The influence of sodium and potassium dynamics on excitability, seizures, and the stability of persistent states: I. Single neuron dynamics. J Comput Neurosci. 2009; 26: 159-170.

What is interesting about this system compared to other experiments that we have done is that this system is not bistable. The system only exists in its bursting state, and it is impossible to suppress the bursting behavior indefinitely. As such, we try to accomplish something a little different. Instead of seeking to suppress the system for a long period, we seek to suppress the burst quicker than normal, while maintaining when the next burst will occur.

The bursting state cycles every 38 seconds, with action potentials firing the first 6 seconds and quiescence in the remaining 32 seconds. Using EDA we sought to give a 2-second stimulus to the system 100 milliseconds after the bursting begins, suppressing any action potentials from occurring for 36 seconds following the end of the stimulus.

Coupled Oscillators Network

From a network perspective, there is a hypothesis that one of the mechanisms underlying epileptic seizures is a synchronization of various regions of the brain. Synchronization has been observed in rat hippocampal slices perfused with high potassium saline solutions. One of the alternative electrical therapies for patients has been vagal nerve stimulation (VNS). While its exact mechanism is still unknown, it is hypothesized that VNS works by desynchronizing neuronal activity, an idea supported by the EEG response to VNS.

As such, we have attempted to model a network of five coupled Hodgkin-Huxley neurons. We chose five for computational purposes, but we could scale up the model relatively easily. In order to model them as oscillators, we have increased the persistent current to 12 μA/cm² such that the system is monostable repetitive firing. We coupled every neuron with every other neuron by using a constant coupling factor and the voltage differences between the neurons:

$$\alpha \sum_{j=1}^{5}(V_i - V_j) \quad (20)$$

where i represents the neuron in question, j represents all neurons and α is the coupling constant. The new model of equations replaces Eq. (1) with:

$$C\dot{V}_i = 120m_i^3 h_i(V_i - 115) - 36n_i^4(V_i + 12) - 0.3(V_i - 10.613) - 12 - \alpha\sum_{j=1}^{5}(V_i - V_j) - u \quad (21)$$

where $V_i$, $m_i$, $n_i$, and $h_i$ are the state variables of the $i^{th}$ neuron. All the other equations still applied.

We started the five neurons in a near synchronous state. We chose to use a 31-ms stimulus duration (two cycle lengths). In this model, the mean-field potential of the five neurons is representative of what an EEG reading. From our white noise snippets, we noted that a very small percentage (0.02%) successfully dropped the mean-field below 32.5 mV. As such, we set up EDA to find the optimal 31-ms stimulus waveform that would take the mean-field potential to below 32.5 mV by the end of the 31 milliseconds.

Population-Based Systemic Bursting

The models of epilepsy can be generally categorized as either microscopic, ionic models and macroscopic, population models. The first three models we have examined fall in the first category, examining and quantifying the ionics of the system. Because epilepsy affects extremely large networks, it is difficult and time-intensive to calculate the ionic mechanism underlying each individual neuron in these large networks. As such, researchers have developed population-based models that lump together groups of neurons into their mean-field components, modeling interactions between populations of neurons as opposed to individual neurons.

Figure 15:
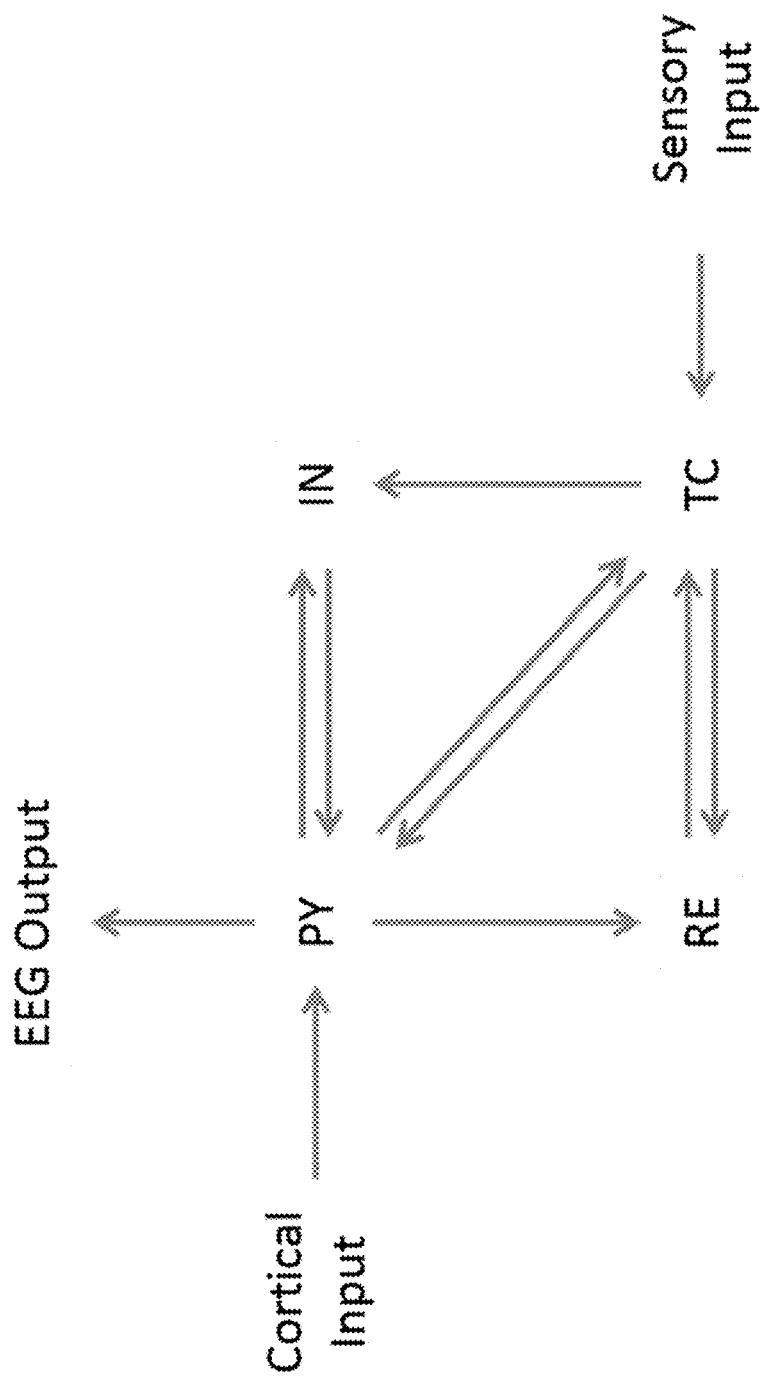
FIG. 15 is a diagram of the Suffczynski et al model, in which four populations of neurons are modeled, including pyramidal neurons (PY), interneurons (IN), reticulothalamic neurons (RE), and thalamocortical neurons (TC). Sensory and cortical inputs are shown as is an EEG output.

For our experiment, we have examined a simple bistable system developed by Suffczynski et al. This model examines epilepsy through the interactions of four populations of neurons: pyramidal neurons, interneurons, thalamocortical neurons and reticulothalamic neurons. In this model, the pyramidal neurons qualitatively mimic EEG activity. FIG. 15 is a diagram of the Suffczynski et al model, in which four populations of neurons are modeled, including pyramidal neurons (PY), interneurons (IN), reticulothalamic neurons (RE), and thalamocortical neurons (TC). Sensory and cortical inputs are shown as is an EEG output. The diagram shows the various interconnections modeled between the four populations of neurons.

The researchers tailored the parameters to match experimental data collected from the Wistar albino Glaxo from Rijs-wijk (WAG/Rij) rat, which is a genetic animal model of absence epilepsy.

In this model, there exist two states, a quiescent state, and a seizure state delineated by the strength of the pyramidal neurons' mean-field voltage. The system can spontaneously transition on its own from one state to the other due to a low level of sensory noise programmed into the model. We found a set of initial conditions for the system such that the system begins in the quiescent state, but then spontaneously transitions into a seizure state a second later. For this model, we used EDA to find the optimal 100-ms waveform that was sufficient to suppress the seizing state back to quiescence within 100 milliseconds after the stimulus terminated.

Suppression of Single Cell Repetitive Firing

FIG. 16A and FIG. 16B show the optimal stimulus found through EDA.

FIG. 16A is a graph of an optimal stimulus waveform for suppressing repetitive firing in a single cell as a function of time.

As seen in FIG. 16A, the optimal stimulus is multi-phasic with a prominent biphasic component in the center. The stimulus is also in anti-phase with the membrane voltage.

FIG. 16B is a graph of the response as a function of time.

As a point of comparison, we did a grid search of biphasic rectangular pulses with varying stimulus duration (1 ms to 20 ms per phase) and stimulus amplitude (−10 µA/cm$^2$ to 10 µA/cm$^2$ for the first phase, the inverse for the second phase, in 0.1 µA/cm$^2$ increments). The optimal rectangular pulse that we found was 2-ms duration per phase, 1.4 µA/cm$^2$ and −1.4 µA/cm$^2$ for the first and second phase respectively and had a total energy usage of 7.84 µJ. The optimal stimulus waveform found using EDA had a total energy usage of 2.63 µJ.

Suppression of Single Cell Bursting

This model of the single cell burster is a little different from the other three models in that the cell is not in a clearly defined repetitive firing state or a quiescent state, but instead in perpetual bursting state. FIG. 17A through FIG. 17C show the optimal 2-second stimulus that successfully suppressed one burst prematurely while maintaining when the next burst occurs.

FIG. 17A is a graph of an optimal 2 second stimulus waveform for suppressing repetitive firing in a single cell burster as a function of time.

FIG. 17B is a graph of the response as a function of time when the optimal stimulus is given.

FIG. 17C is a graph of the response as a function of time when no stimulus is given.

What is difficult to see in FIG. 17B and FIG. 17C is that there are 168 action potentials occurring both when the stimulus is given and when the stimulus is not given. We discuss this result further in the discussion.

Desynchronization of Coupled Oscillators

Figures 18A, 18B:
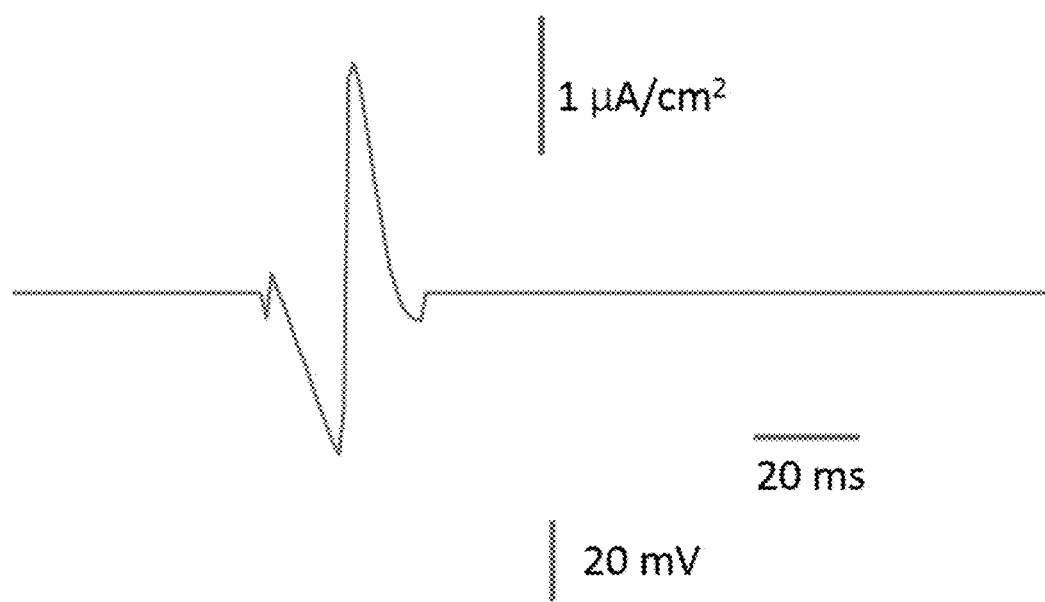
FIG. 18A is a graph of an optimal stimulus waveform for desynchronizing a network of coupled oscillators.
FIG. 18B is a graph showing the response, in which the oscillators are decoupled by the application of the stimulus waveform of FIG. 18A.

From the perspective of a network of coupled oscillators, we again see a biphasic stimulus that is in antiphase to the system as seen in FIG. 18A and FIG. 18B.

FIG. 18A is a graph of an optimal stimulus waveform for desynchronizing a network of coupled oscillators.

FIG. 18B is a graph showing the response, in which the oscillators are decoupled by the application of the stimulus waveform of FIG. 18A.

It is interesting to note that the timing of the stimulus as it relates to the phase of the neurons is extremely important. We see that the stimulus leverages the slight differences between the oscillators to time the stimulus just right so that each one responds slightly differently compared to the others, causing desynchronization.

For this model, we also did a rectangular pulse grid search and found that the optimal rectangular waveform had an $L^2$-norm of 154.88 µJ/cm$^2$ as compared to the optimal determined by EDA which had an $L^2$-norm of 11.80 µJ/cm$^2$.

Suppression of Systemic Bursting

FIG. 19A and FIG. 19B show the optimal stimulus waveform found by EDA for the population-based model of systemic bursting.

FIG. 19A is a graph showing the stimulus, the system's response, and the control response with no stimulus for an optimal stimulus waveform for suppressing seizure activity in a systemic population-based model.

FIG. 19B is a graph showing a detailed view of the transition due to the stimulus shown in FIG. 19A.

As we can see, the solution does indeed suppress the seizure state and bring it back to quiescence. Again, we see the biphasic nature of the stimulus in antiphase to the voltage membrane of the pyramidal neurons.

Electrical Stimulation for Epileptic Treatment

Research has shown that 30% of all patients suffering from epilepsy do not see a reduction of seizure activity on anti-epileptic drugs. While surgical procedures are an alternative form of treatment for patients, not all of them are capable of undergoing those procedures. As such, researchers have looked into brain stimulation as a method to help in the suppression of epileptic seizures.

Today, there are three types of brain stimulation that clinicians use to treat epilepsy: vagus nerve stimulation, deep brain stimulation, and responsive neural stimulation.

The traditional brain stimulation waveform for these therapies is rectangular. In order to tailor the stimulation for each patient, clinicians adjust a limited set of parameters including pulse duration, pulse frequency, and pulse amplitude to reduce adverse effects and maximize efficacy.

From a computational perspective, there is growing interest in applying non-standard pulsatile stimulation for the treatment of epilepsy. Wilson and Moehlis have applied mathematical techniques and principles to solving computational models of epilepsy to find energetically efficient stimuli to terminate seizure-like bursting behavior to a reduced version of the Cressman model. Tass has examined the use of delayed feedback stimulation as a method to suppress seizures, but he does not examine it from the perspective of energy-efficiency.

Rectangular Pulses are not Optimal

We have captured the optimal stimulus waveform using EDA on four separate computational models of epilepsy: suppression of single cell repetitive firing, desynchronization of networked coupled oscillators, suppression of systemic bursting and suppression of single cell bursting. We have shown in the first two models that the optimal solution performs much better than optimal rectangular waveforms, thus allowing for potentially large energy reductions in energy consumption. This improvement in energy consumption makes sense from the perspective that the biological world responds more often to signals bandlimited by certain frequencies. From a signals perspective, sharp edges in the stimulus require extremely high frequencies, and thus these frequencies are wasted energy when given to a system that does not respond to such extreme rates of change.

Optimal Stimulus Waveforms are Short Discrete Bursts in Antiphase to the System

The field of dynamical system theory has studied effect of short discrete pulses in the context of oscillatory systems. Some of the research has focused on examining how these short discrete bursts have changed the phase settings of the system, while others have examined how short discrete bursts can be used to desynchronized coupled oscillator networks or completely suppress oscillations. Here in our study, we have seen that in all four models, a short discrete burst of stimuli, when given at the proper time with the proper waveform, can rectify the dysfunctional oscillatory activity that we see during seizure activity.

Furthermore, we also note that for three of the models (suppression of single cell repetitive firing, desynchronization of coupled oscillators and suppression of systemic bursting), the optimal stimulus waveform is in antiphase with the system's internal oscillation, indicating that optimally effective stimuli are phase-dependent. The same stimulus waveform may not work if given at a different phase, or time in the cycle. While the idea that antiphasic stimuli has a suppressive relationship with an oscillatory system is well-known in dynamical systems theory, it is slowly gaining traction in the field of neuroscience as well. Rosenblaum and Pikovsky, as well as others later, demonstrated how synchronization can be controlled via a delayed-feedback stimulus that is slightly out of phase with the system. More recently, computational studies have found optimal stimuli that are not just slightly out of phase, but in complete antiphase with the system's oscillations.

Mechanistically, if we examine the suppression of the repetitive firing of the single cell Hodgkin-Huxley, we can observe that the optimal stimulus gives a brief depolarization pulse followed by a larger hyperpolarization pulse. The hyperpolarization pulse when the system would normally be building towards the action potential. We have seen this result occur before in the suppression of repetitive firing in the FitzHugh-Nagumo model as seen in the results from U.S. Ser. No. 62/139,014.

We also see this mechanism of suppressing repetitive firing at the system level bursting. We see that the stimulus given is in antiphase with the system such that it counteracts the oscillations, suppressing the burst.

This concept of stimulating in antiphase is intuitive for most people. As most people will know, one of the gentlest ways to stop somebody on a swing is to apply opposing pressure on the swing to counteract the force by the child. The same principles apply here: the stimulus is a depolarizing and hyperpolarizing force gently stopping the system from continuing on its oscillatory state.

At first glance, the desynchronization of the coupled oscillator network is different from the other two models. What is important to remember here is that the neurons are monostable repetitive firing. It is impossible to suppress these neurons to complete quiescence. When we examine what is happening, we note that the stimulus is in antiphase again with the system as we have seen in the other two models. However, because the system is stable only in the repetitive firing state, the neuron will inevitably return to repetitive firing. In the attempt to suppress the neuron, the stimulus does cause a slight delay in between firing. The slight differences in phase with respect to the timing of the stimulus lead to the dispersion of phase across the different oscillators.

The fact that the stimuli are all in antiphase with the system indicates that the stimulus is phase-dependent, meaning that the stimulus needs to be given at exact times with respect to the system. If the stimulus was in phase with the system, one could hypothesize that the stimulus may actually amplify the seizures, causing further debilitation and other detrimental side effects.

With more research, we may be able to one day develop therapeutic devices that can measure the phase and the frequency of the epileptic dysfunctional oscillations and calculate the proper parameters for the waveform to minimize detrimental side effects while maximizing efficacy. Furthermore, by using an adaptive algorithm, these devices could potentially even adapt to changes in the phase or frequency of the system due to physiologically changes in the patient.

Understanding the Single Cell Burster

The single-cell bursting model poses an interesting challenge, as it appears to be an exception to the theme in that the optimal stimulus waveform does not match what we have seen in the other three models. When examining the bursting system, we note that there is a fast wave and a slow wave. The fast wave dictates the firing of the action potentials during the repetitive firing phase and the slow wave dictates whether the cell is in the repetitive firing phase or the quiescent phase of the bursting cycle. From what we can see, our stimulus is on a much slower time scale and thus appears to suppress the bursting behavior by affecting the slow part of the burster.

We also note that while the last action potential in the repetitive firing phase ends much sooner than the control, the stimulus fires as many action potentials as the control. When examining the other state variables, it would seem that the stimulus pushes the system around the limit cycle quicker in order to suppress the repetitive firing portion sooner. From a clinical perspective, this may not be of much benefit to the patient, as it would appear that the stimulus seems to magnify the epileptic seizure first before suppressing it.

We did try running the same algorithm using an extremely small 20-ms stimulus in order to match the fast part of the bursting model. Unfortunately, we were unable to capture any successful stimuli in our search. This would imply that it is easier to affect the suppression of the bursting behavior by targeting the slow component as opposed to the fast component. Because of computational limitations, we have not yet been able to run a long high-resolution stimulus targeting both fast and slow waves simultaneously in order to determine whether the optimal stimulus waveform can benefit by affecting both components.

While the antiphasic feature does not appear in the single cell burster, it is possible that through exploring higher resolution stimuli with EDA, we will find a stimulus that exists in antiphase to the fast wave and thus confirm the pattern we have seen in the other three models. For that matter, if we were to run a much longer stimulus, we may also see the antiphasic properties appear in relation to the slow wave. From a patient's perspective, a weak, but prolonged stimulus may not be desirable compared to a strong, but short stimulus. It may also be interesting to examine a long stimulus with extremely high resolution to be examine both the fast wave and the slow wave components at the same time. This would be a computational challenge, but it may give us unique insight into how the different components play a role in the suppression of epileptic seizures.

Figure 20:
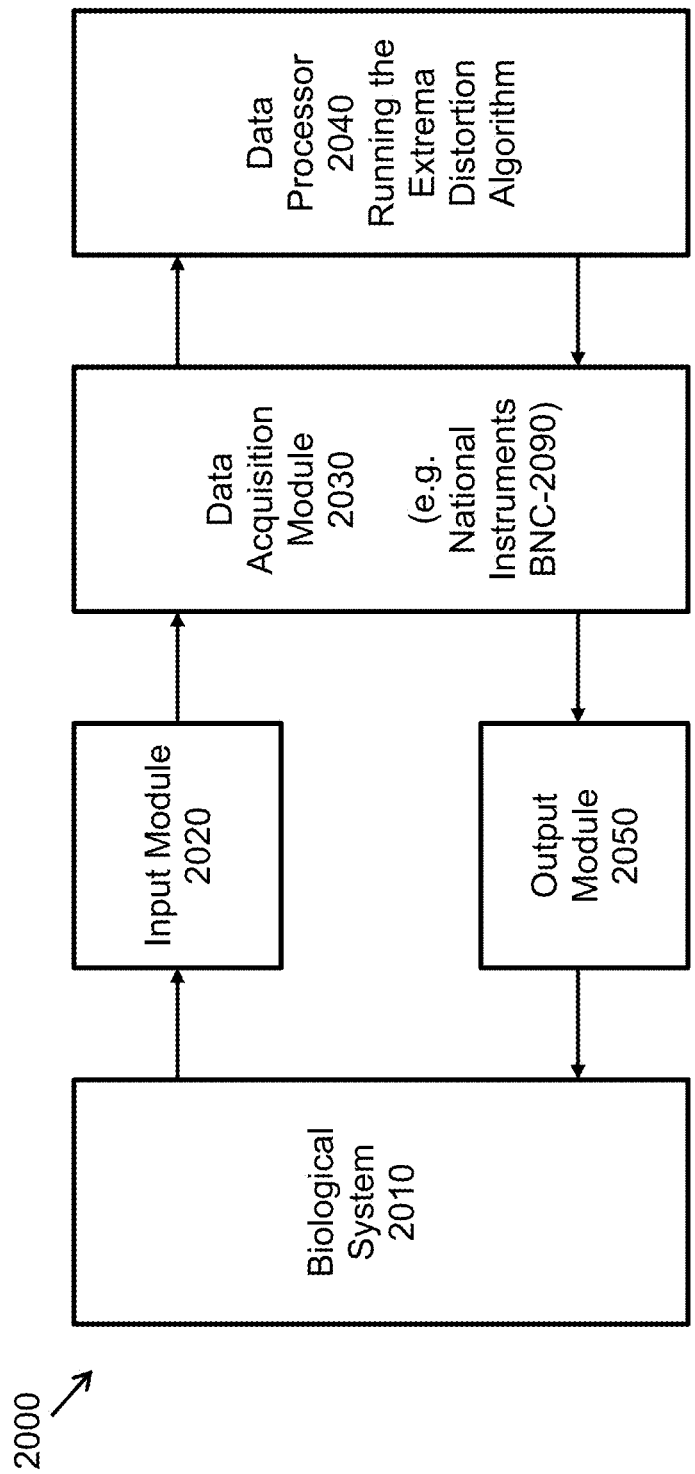
FIG. 20 is a schematic diagram of an apparatus and system 2000 that implements the Extrema Distortion Algorithm according to the principles of the invention.

FIG. 20 is a schematic diagram of an apparatus and system 2000 that implements the Extrema Distortion Algorithm according to the principles of the invention.

As shown in FIG. 20 a biological system 2010 is to be examined and controlled with a stimulus. The biological system 2010 can be a cell, an animal, or a human subject, or a specific part of the animal or human subject, such as a limb, an organ, a part of the neurological system such as a nerve or the brain, or a sensory organ such as an eye, an ear, a nose, a tongue or a region of a surface of the animal or human, such as the skin. The biological system 2010 is interfaced with an input module 2020 that receives signals from the biological system, or the region of interest in the biological system. The received signals can be electrical signals, chemical signals, mechanical signals, or auditory signals, and combinations thereof.

The input module 2020 processes the signals received from the biological system 2020. In one embodiment, the input module provides output signals in the form of analog (continuous) signals having an amplitude and a phase, such as analog electrical; signals. In another embodiment, the input module provides output signals in the form of a plurality of discrete (e.g., digital) time based signals, each discrete signal having an amplitude and an identifier indicating the position of the signal in a time sequence. As will be understood by those of ordinary skill in the art, the signals that are received from the biological system 2010, once converted to electrical signals, can be recorded in a memory. Without limiting the generality of discussion, signals can also be recorded by each of the subsequent data acquisition, data processing, and/or output modules that are described herein, such as by the simple expedient of providing a USB based memory module, such as a thumb drive or memory stick in any such module where data recording is desired.

The input module 2020 communicates it output signals to a data acquisition module 2030. In some embodiments, the data acquisition module is a National Instruments BNC-2090, available from National Instruments Corporation, 11500 Mopac Expwy, Austin, Tex. 78759-3504. In general, the data acquisition module 2030 can receive signals from the input module 2020 and can communicate with a data processor 2040 running the Extrema Distortion Algorithm.

In some embodiments, a data processor 2040 can be a general purpose programmable computer, which is described in further detail hereinbelow. By way of example, a suitable general purpose programmable computer can be a laptop personal computer (PC), a desktop PC, or a server, for example a laptop PC such as one available from \vendors such as Dell, Lenovo, and Apple.

The data processor 2040 applies the Extrema Distortion Algorithm as part of a computational process to the data received from the data acquisition module 2030. Once the result of the computational process is obtained, the result is communicated by way of the data acquisition module 2030 to an output module 2050 that interfaces with the biological system, the output module 2050 applies a stimulus to the biological system 2010. The stimulus that is applied is generated based at least in part on the result of the computation that includes application of the Extrema Distortion Algorithm.

In some embodiments, the process of receiving data from the biological system 2010, processing the data in a data processor 2040 running the Extrema Distortion Algorithm as part of a computational process and applying the resultant signal to the biological system 2010 can be iterated as many times as desired.

In some embodiments, the process of receiving data from the biological system 2010, processing the data in a data processor 2040 running the Extrema Distortion Algorithm as part of a computational process and applying the resultant signal to the biological system 2010 can be operated in a manner that monitors the received data and generates a response signal to be applied only when the input data indicates that the biological system 2010 is behaving abnormally, and does not apply a response signal when the biological system 2010 is behaving normally.

Figure 21:
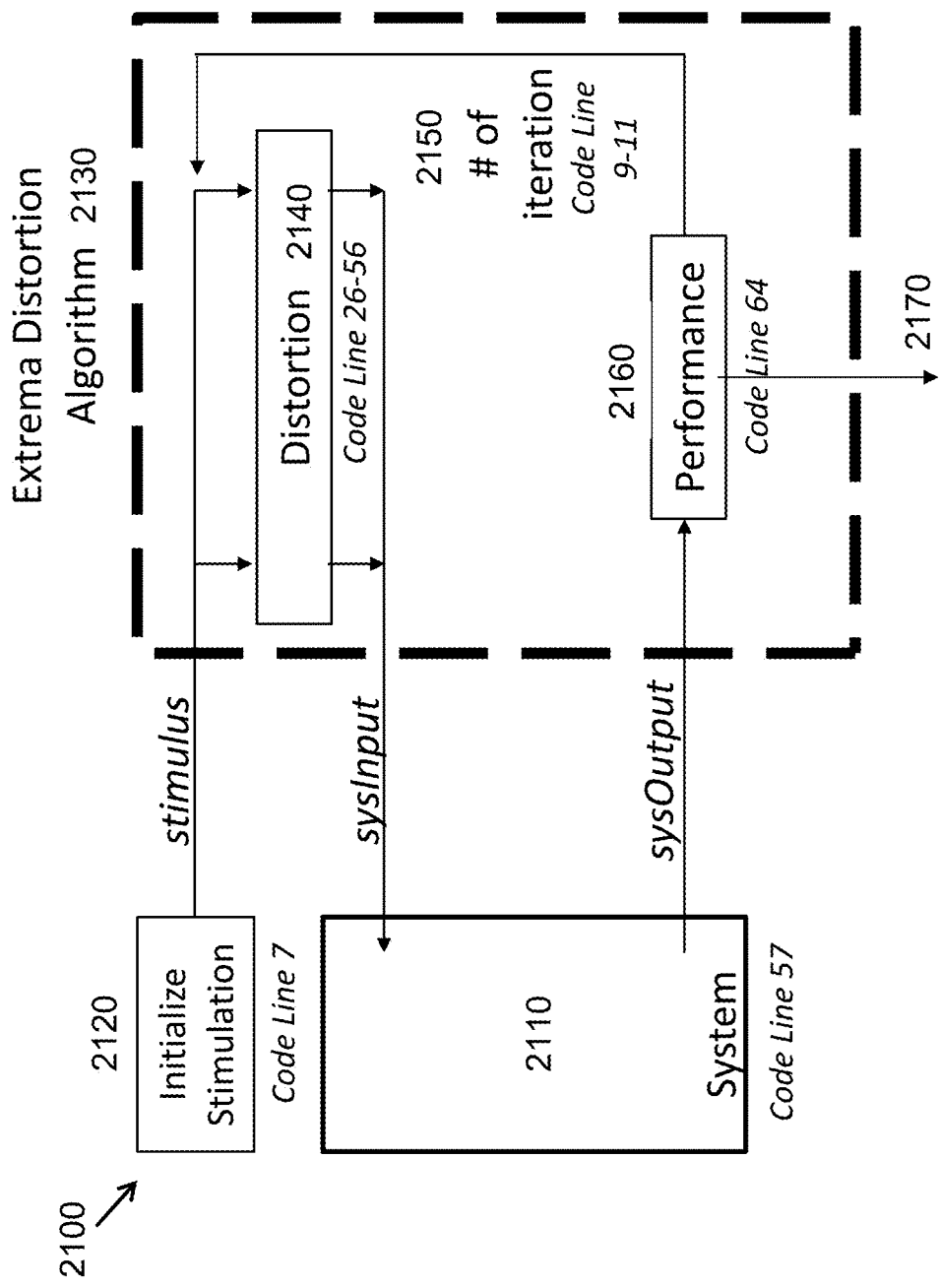
FIG. 21 is a schematic flow diagram 2100 that illustrates the operation of the Extrema Distortion Algorithm as part of a computational process. A text file containing the code of the Extrema Distortion Algorithm is provided herewith as part of the present description.

FIG. 21 is a schematic flow diagram 2100 that illustrates the operation of the Extrema Distortion Algorithm as part of a computational process. a text file containing the code of the Extrema Distortion Algorithm is provided herewith as part of the present description. As illustrated in FIG. 21, a stimulation of a system 2110 of interest, such as a biological system previously described, begins with an initialization. Step 2120 initialize stimulation is such an initialization.

An initialized stimulus is communicated to the Extrema Distortion Algorithm 2130 and is received by a distortion module 2140, as indicated by the arrow labeled "stimulus."

The system 2110 provides a signal, indicated by the arrow labeled "sysOutput" to the Extrema Distortion Algorithm 2130. The Extrema Distortion Algorithm 2130 uses a Perfromance module 2160 to analyze the sysOuptut signal. The result of the analysis may be delivered to a user (or to another process) as indicated by the arrow 2170. Based on the analysis, a signal is sent from the performance module 2060 to the distortion module 2140 as indicated by the arrow labeled # of iteration 2150. An iteration counter records the number of the iteration, starting with an initialized value of 0 (n=0), so that the first such communication increments the counter, indicating that one iteration (n=1) has been performed.

The distortion module uses the stimulus signal and the performance signal to generate a signal to be communicated to the system 2110, which signal is indicated by the arrow labeled sysInput.

FIG. 21 also has indicated thereon where (by line number) the various steps in the application of the Extrema Distortion Algorithm 2130 perform the various operations described herein.

Figure 22:
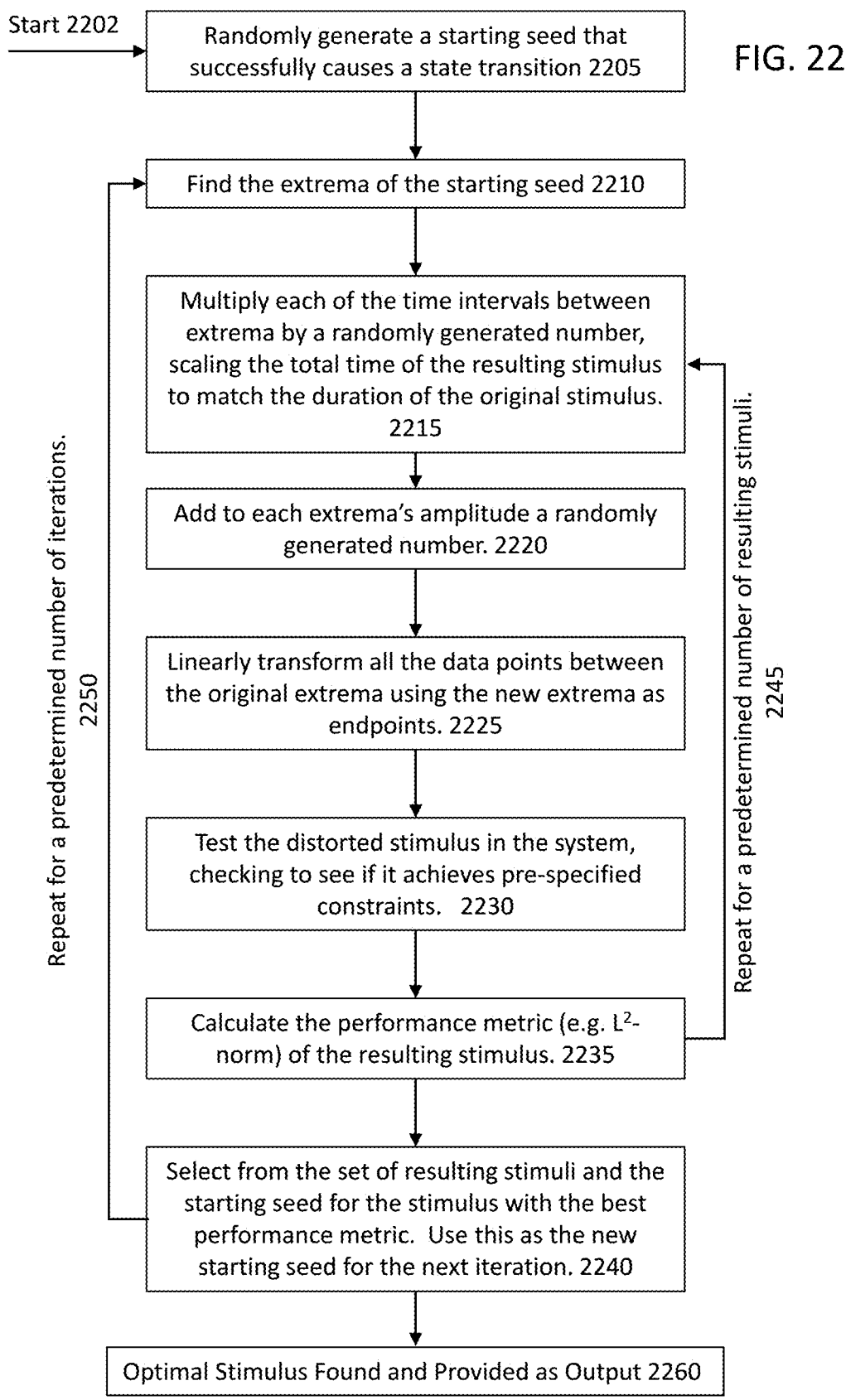
FIG. 22 is a schematic diagram illustrating the steps in the Extrema Distortion Algorithm.

FIG. 22 is a schematic diagram illustrating the steps in the Extrema Distortion Algorithm.

The process starts at step 2202. In step 2205 the process randomly generates a starting seed that successfully causes a state transition. In step 2210 the process finds the extrema of the starting seed. In step 2215 the process multiplies each of the time intervals between extrema by a randomly generated number, scaling the total time of the resulting stimulus to match the duration of the original stimulus. In step 2220 the process adds to each extrema's amplitude a randomly generated number. In step 2225 the process linearly transforms all the data points between the original extrema using the new extrema as endpoints. In step 2230 the process tests the distorted stimulus in the system, checking to see if it achieves pre-specified constraints. In step 2235, the process calculates the performance metric (e.g. $L^2$-norm) of the resulting stimulus. Steps 2215 through 2235 are repeated a predetermined number of instances to generate the first set of neighboring solutions. The neighboring solutions are compared to the starting seed via their performance metric. In step 2240 the process selects the best solution from the set of neighboring solutions and the starting seed as the starting seed for the next iteration. If fewer than a predetermined number of iterations M, where M is an integer greater than 1, have been performed the process then follows arrow 2250 back to step 2210. When step 2240 has been reached a total of M times, the optimal stimulus has been found and is provided as output at step 2260.

Definitions

Any reference in the claims to an electronic signal or an electromagnetic signal (or their equivalents) is to be understood that in a preferred embodiment the signal is a non-transitory electronic signal or a non-transitory electromagnetic signal. If the signal per se is not claimed, the reference may in some instances be to a description of a propagating or transitory electronic signal or electromagnetic signal.

Recording the results from an operation or data acquisition, such as for example, recording results at a particular frequency or wavelength, is understood to mean and is defined herein as writing output data in a non-transitory or non-volatile manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A system for controlling a signaling pathway in a subject of interest, comprising:
    a sensor configured to observe a signal in the subject of interest, and configured to provide an electrical representation of said signal for further manipulation;
    a module configured to accept as input said electrical representation of said signal for further manipulation;
    a module configured to apply the Extrema Distortion Algorithm to said electrical representation of said signal, and configured to generate a synthetic control signal;
    a module configured to provide said synthetic control signal as an output; and
    a signal application module configured to receive said synthetic control signal and configured to apply said synthetic control signal to the subject of interest, wherein
    said module configured to apply the Extrema Distortion Algorithm is a general purpose programmable computer which when operating under control of instructions recorded on a non-volatile medium is configured to perform the steps of said Extrema Distortion Algorithm, and
    said Extrema Distortion Algorithm includes instructions recorded on said non-volatile medium that are configured to direct said general purpose computer to: (a) Select a randomly generated starting seed that successfully causes a state transition, (b) Find the extrema of the starting seed and measure the time interval between them, (c) Multiply each of the time intervals by a randomly generated number (e.g. with a Gaussian distribution), (d) Rescale the time of the synthetic stimulus to match the duration of the original stimulus, (e) Add to each peak a randomly generated number (e.g. with a Gaussian distribution), (f) Linearly transform all the data points between the extrema with the new extrema endpoints, (g) Test the distorted stimulus in the system, checking to see if it achieves pre-specified constraints, (h) Calculate the performance metric (e.g. $L^2$-norm) of each of the neighboring stimuli, (i) Repeat steps (c)-(h) N times to produce N neighboring solutions based on the starting seed, (j) Choose the stimulus from among the neighboring solutions and the starting seed with the best performance, (k) Repeat steps (b)-(j) for a predetermined number of times M each iteration using the best stimuli found from the previous iteration as the new starting seed in step (b), and (l) After M iterations, output the stimulus with the best performance metric as the optimal stimulus.

2. The system for controlling a signaling pathway in a subject of interest of claim 1, wherein said sensor configured to observe a signal is configured to provide said electrical representation in the form of an analog signal having an amplitude and a phase.

3. The system for controlling a signaling pathway in a subject of interest of claim 1, wherein said sensor configured to observe a signal is configured to provide said electrical representation in the form of a plurality of discrete time based signals, each discrete signal having an amplitude and an identifier indicating the position of the signal in a time sequence.

4. The system for controlling a signaling pathway in a subject of interest of claim 1, wherein said module configured to accept as input said electrical representation is a data acquisition module.

5. The system for controlling a signaling pathway in a subject of interest of claim 1, wherein said module configured to provide said synthetic control signal as an output is a data acquisition module having a data output port.

* * * * *